US008603357B2

(12) United States Patent
Sakamoto et al.

(10) Patent No.: US 8,603,357 B2
(45) Date of Patent: Dec. 10, 2013

(54) POLYMERIZABLE CHIRAL COMPOUND, POLYMERIZABLE LIQUID CRYSTAL COMPOSITION, LIQUID CRYSTAL POLYMER AND OPTICALLY ANISOTROPIC BODY

(75) Inventors: Kei Sakamoto, Tokyo (JP); Kentaro Tamura, Tokyo (JP)

(73) Assignee: Zeon Corporation, Tokyo (JP)

( * ) Notice: Subject to any disclaimer, the term of this patent is extended or adjusted under 35 U.S.C. 154(b) by 255 days.

(21) Appl. No.: 13/121,747

(22) PCT Filed: Sep. 9, 2009

(86) PCT No.: PCT/JP2009/065731
§ 371 (c)(1),
(2), (4) Date: Apr. 15, 2011

(87) PCT Pub. No.: WO2010/038591
PCT Pub. Date: Apr. 8, 2010

(65) Prior Publication Data
US 2011/0186777 A1  Aug. 4, 2011

(30) Foreign Application Priority Data
Oct. 1, 2008  (JP) ................ 2008-256855

(51) Int. Cl.
C09K 19/52 (2006.01)
C09K 19/34 (2006.01)
C09K 19/06 (2006.01)
C09K 19/00 (2006.01)
G02F 1/1333 (2006.01)
C07D 493/00 (2006.01)
C07D 307/77 (2006.01)
C07D 321/00 (2006.01)

(52) U.S. Cl.
USPC ............. 252/299.6; 252/299.01; 252/299.61; 428/1.1; 349/1; 349/56; 349/86; 349/182; 549/200; 549/429; 549/456; 549/462; 549/464

(58) Field of Classification Search
USPC ............. 252/299.01, 299.6, 299.61; 549/200, 549/429, 456, 462, 464; 428/1.1; 349/1, 56, 349/86, 182
See application file for complete search history.

(56) References Cited

U.S. PATENT DOCUMENTS

| | | |
|---|---|---|
| 5,506,704 A | 4/1996 | Broer et al. |
| 5,593,617 A | 1/1997 | Kelly et al. |
| 5,737,044 A | 4/1998 | Van Haaren et al. |
| 5,744,057 A | 4/1998 | Meyer et al. |
| 5,822,029 A | 10/1998 | Davis et al. |
| 6,010,642 A | 1/2000 | Takatsu et al. |
| 6,180,028 B1 | 1/2001 | Hotaka et al. |
| 6,468,444 B1 | 10/2002 | Meyer et al. |
| 6,680,003 B2 | 1/2004 | Chuard et al. |
| 2003/0026922 A1 | 2/2003 | May et al. |
| 2003/0072893 A1 | 4/2003 | Nakano et al. |
| 2003/0219548 A1 | 11/2003 | Meyer et al. |
| 2004/0232383 A1 | 11/2004 | Imamoto et al. |
| 2010/0258764 A1 | 10/2010 | Sakamoto et al. |

FOREIGN PATENT DOCUMENTS

| | | |
|---|---|---|
| EP | 0606940 A2 | 7/1994 |
| EP | 0720041 A2 | 7/1996 |
| GB | 2312529 A | 10/1997 |
| GB | 2 330 139 A | 4/1999 |
| JP | 62-70406 A | 3/1987 |
| JP | 8-104870 A | 4/1996 |
| JP | 9-20781 A | 1/1997 |
| JP | 9-31077 A | 2/1997 |
| JP | 10-147562 A | 6/1998 |
| JP | 11-71338 A | 3/1999 |
| JP | 11-100575 A | 4/1999 |
| JP | 11-130729 A | 5/1999 |
| JP | 11-193287 A | 7/1999 |
| JP | 2000-309589 A | 11/2000 |
| JP | 2002-241757 A | 8/2002 |
| JP | 2002-265421 A | 9/2002 |
| JP | 2002-308832 A | 10/2002 |
| JP | 2002-533742 A | 10/2002 |
| JP | 2003-137887 A | 5/2003 |
| JP | 2005-505577 A | 2/2005 |
| JP | 2005-263789 A | 9/2005 |
| JP | 2005-309255 A | 11/2005 |
| JP | 2007-269640 A | 10/2007 |
| JP | 2008-170835 A | 7/2008 |
| JP | 2008-291218 A | 12/2008 |
| JP | 2009-167378 A | 7/2009 |
| WO | WO 96/02016 A2 | 1/1996 |
| WO | WO 98/08135 A1 | 2/1998 |
| WO | WO 00/37585 A1 | 6/2000 |
| WO | WO 2008/133290 A1 | 11/2008 |
| WO | WO 2009/078431 A1 | 6/2009 |

OTHER PUBLICATIONS

International Search Report, dated Oct. 27, 2009 issued in PCT/JP2009/065731.
McLoughlin et al., "Azines: conjugation stoppers or conjugation switches", Journal of Materials Chemistry, vol. 17, No. 40, Aug. 17, 2007, pp. 4304-4308.
Perez Jubindo et al., "Dielectric and Optical Measurements for Some Compounds Exhibiting an IS-Ch-Smc* Phase Transition Sequence", Molecular Crystals and Liquid Crystals, vol. 159, 1988, pp. 137-149.
Alam et al., "The influence of molecular structure on helical twisting power of chiral azobenzene compounds," Liquid Crystals, vol. 34, No. 10, Oct. 2007, pp. 1215-1219, XP001507801.
Extended European Search Report dated Apr. 20, 2012 for European Application No. 09817628.2.

*Primary Examiner* — Geraldina Visconti
(74) *Attorney, Agent, or Firm* — Birch, Stewart, Kolasch & Birch, LLP

(57) ABSTRACT

The present inventions to provide a novel polymerizable chiral compound (chiral agent) having high helical twisting power, a polymerizable liquid crystal composition comprising the polymerizable chiral compound and a polymerizable liquid crystal compound, a liquid crystal polymer, and an optically anisotropic body. The object was achieved by a polymerizable chiral compound represented by the following formula (I), a polymerizable liquid crystal composition comprising the polymerizable chiral compound and a polymerizable liquid crystal compound, a liquid crystal polymer, and an optically anisotropic body:

[Chemical formula 1]

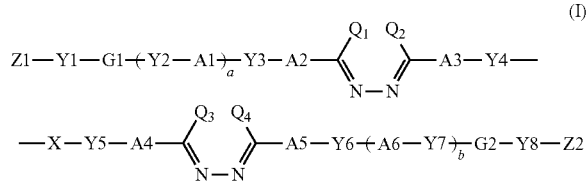

(I)

wherein Y1 to Y8 are each —O—, —O—C(=O)—, —C(=O)—O— or the like; G1 and G2 are each a divalent aliphatic group having 1 to 20 carbon atoms or the like; Z1 and Z2 are each an alkenyl group having 2 to 10 carbon atoms or the like; $Q_1$ to $Q_4$ are each a hydrogen atom or the like; A1 to A6 are each a divalent aromatic group A having 6 to 30 carbon atoms; and X is any of groups represented by the following (X-i) to (X-vi):

[Chemical formula 2]

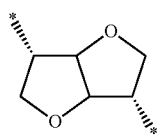

(X-i)

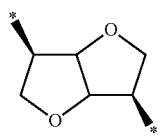

(X-ii)

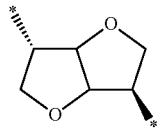

(X-iii)

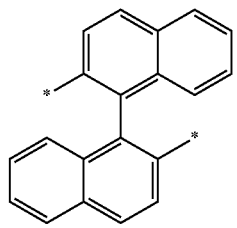

(X-iv)

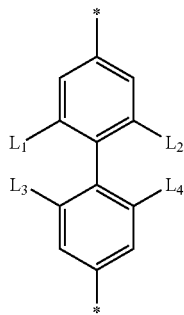

(X-v)

(X-vi)

wherein * represents a bond and $L_1$ to $L_4$ are each an alkyl group having 1 to 4 carbon atoms or the like;

and wherein, in the formula (I), a and b are each 0 or 1.

10 Claims, No Drawings

POLYMERIZABLE CHIRAL COMPOUND, POLYMERIZABLE LIQUID CRYSTAL COMPOSITION, LIQUID CRYSTAL POLYMER AND OPTICALLY ANISOTROPIC BODY

TECHNICAL FIELD

The present invention relates to a novel polymerizable chiral compound having high helical twisting power, a polymerizable liquid crystal composition comprising the polymerizable chiral compound, a liquid crystal polymer obtained by polymerization of the polymerizable liquid crystal composition, and an optically anisotropic body comprising the liquid crystal polymer as a constitutional material.

BACKGROUND ART

A resin layer having cholesteric regularity (hereinafter, it will be referred to as "cholesteric resin layer") has a characteristic of reflecting a circular polarized light which is in a rotational direction that is the same as the direction of helical rotation of cholesteric regularity (hereinafter, the characteristic will be referred to as "selective reflection characteristic").

A wavelength range which exhibits the selective reflection characteristic depends on the period of cholesteric regularity. By increasing the distribution width of the period of cholesteric regularity, it is possible to increase the width of the wavelength range which exhibits the selective reflection characteristic (hereinafter, it will be referred to as "selective reflection band").

If it is possible to form a circularly polarized light separating sheet comprising a cholesteric resin layer having the selective reflection band in the visible light wavelength range, of natural incident light, the circularly polarized light separating sheet reflects only the circularly polarized light of a specific wavelength and transmits circularly polarized lights of other wavelength. Reutilization of the reflected light is possible by allowing the same to re-enter to the resin layer using a reflector, etc. Also, it is possible to convert natural light to linearly polarized light with high efficiency by using the circularly polarized light separating sheet in combination with a quarter-wave plate. Furthermore, a high-luminance liquid crystal display device can be obtained by aligning the direction of the linearly polarized light with the transmission direction of an absorption-type polarizer of a liquid crystal display device, comprising polyvinyl alcohol, etc.

To form the cholesteric resin layer having the selective reflection band in the visible light wavelength range, various chiral agents have been studied.

For example, Patent Literature 1 discloses a chiral compound represented by the formula $(Z^{11}-Y^{11}-A^{11}-O-CO-O-M^{11}-Y^{12})r^1X^a$ wherein $A^{11}$ is a spacer; $M^{11}$ is a mesogenic group; $Y^{11}$ and $Y^{12}$ are chemical bonds or $-O-$, $-S-$, $-CO-O-$, $-O-CO-$, $-O-CO-O-$, $-CO-N(R^a)-$ or $-N(R^a)-CO-$; $X^a$ is $r^1$-valent chiral radical; $R^a$ is hydrogen or $C_1$-$C_4$-alkyl; $r^1$ is from 2 to 6; and $Z^{11}$ is: a1) at least one of these radicals is a reactive group which can participate in a polyaddition reaction, a2) at least two of these radicals are substituents carrying a reactive group which can participate in a polycondensation reaction, b1) is hydrogen or an unreactive radical so long as condition (a1) or (a2) is satisfied.

Patent Literature 2 discloses a chiral compound represented by the formula: $(Z^{12}-Y^{13}-A^{12}-Y^{14}-M^{12}-Y^{15}) r^2X^b$ wherein $A^{12}$ is a spacer; $M^{12}$ is a mesogenic group; $Y^{13}$ to $Y^{15}$ are chemical bonds or $-O-$, $-S-$, $-CO-O-$, $-O-CO-$, $-O-CO-O-$, $-CO-NR^b-$ or $-NR^b-CO-$; $R^b$ is hydrogen or $C_1$-$C_4$-alkyl; $X^b$ is $r^2$-valent chiral group; $r^2$ is 2 to 6; and $Z^{12}$ is: (a3) at least one of these groups is a group with isocyanate, isothiocyanate, cyanate, thiirane, aziridine, carboxyl, hydroxyl or an amino group, (b2) the other group (s) is/are hydrogen or unreactive group.

Patent Literature 3 discloses a compound represented by the formula: $(Z^{13}-Y^{16}-[A^{13}]r^3-Y^{17}-M^{13}-Y^{18}-)r^4X^c$ wherein $A^{13}$ is a spacer; $M^{13}$ is a mesogenic group containing two phenylene radicals which are unsubstituted or substituted by $C_1$-$C_4$-alkyl, methoxy, ethoxy, fluorine, chlorine, bromine, $C_1$-$C_{20}$-alkoxycarbonyl or $C_1$-$C_{20}$-alkylcarbonyl and are linked via $-O-$, $-CO-$, $-CO-O-$, $-O-CO-O-$ or $-CO-O-$; $Y^{16}$ to $Y^{18}$ are direct bonds, $-O-$, $-S-$, $-CO-O-$, $-O-CO-$, $-O-CO-O-$, $-CO-N(R^c)-$ or $-N(R^c)-CO-$; $Z^{13}$ is a polymerizable group; $r^3$ is 0 or 1; $r^4$ is from 2 to 6; $X^c$ is a chiral group; and $R^c$ is $C_1$-$C_4$-alkyl or hydrogen.

Patent Literature 4 discloses a chiral dopant represented by the formula $Z^{14}-Y^{19}-(A^{14})r^5-Y^{20}-M^{14}-Y^{21}-X^d-Y^{22}-(A^{15})r^6-Y^{23}-Z^{15}$ wherein the substituents and variables have the following meanings: $A^{14}$ and $A^{15}$ are each a spacer with a chain length of 1 to 30 C atoms; $Y^{19}$ to $Y^{23}$ are each a chemical bond, $-O-$, $-S-$, $-C(=O)-$, $-C(=O)-O-$, $-O-C(=O)-$, $-CH=CH-C(=O)-O-$, $-O-C(=O)-O-$, $-C(=O)-NR^d-$, $-NR^d-C(=O)-$, $-CH_2-O-$, $-O-CH_2-$, $-CH=N-$, $-N=CH-$ or $-N=N-$; $M^{14}$ is a mesogenic group; $R^d$ is hydrogen or $C_1$-$C_4$-alkyl; $Z^{14}$ and $Z^{15}$ are each hydrogen, $C_1$-$C_4$-alkyl, a polymerizable group or a radical having a polymerizable group; $X^d$ is a dianhydrohexitol residue selected from the group consisting of dianhydrosorbitol, dianhydromannitol and dianhydroiditol; $r^5$ and $r^6$ are 0 or 1; where the radicals $Z^{14}$, $Z^{15}$, $Y^{19}$ to $Y^{23}$, $A^{14}$ and $A^{15}$, can be identical or different, and at least one $Z^{14}$ or $Z^{15}$ radical is a polymerizable group or a radical comprising a polymerizable group.

Patent Literature 5 discloses that the isosorbide derivative typified by the compound represented by the following formula 1 is useful as a chiral dopant:

[Chemical formula 1]

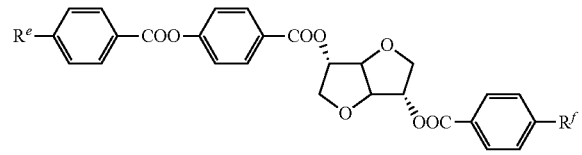

wherein $R^e$ and $R^f$ are Ps-Sp-X, F, Cl, Br, I, CN, SCN, $SF_5$, or a straight chain or branched alkyl with 1 to 30 carbon atoms that is unsubstituted, mono- or poly-substituted by F, Cl, Br, I or CN, and wherein one or more non-adjacent $CH_2$ groups are optionally replaced by $-O-$, $-S-$, $-NH-$, $-NR^g-$, $-CO-$, $-COO-$, $-OCO-$, $-OCO-O-$, $-S-CO-$, $-CO-S-$, $-CH=CH-$ or $-C\equiv C-$ in a manner that O and/or S atoms are not linked directly to one another; $R^g$ is H or alkyl with 1 to 4 carbon atoms; Ps is a polymerizable group; Sp is a spacer group or a single bond; $X^e$ is $-O-$, $-S-$, $-OCH_2-$, $-CH_2O-$, $-CO-$, $-COO-$, $-OCO-$, $-OCO-O-$, $-CO-NR^g-$, $-NR^g-CO-$, $-OCH_2-$, $-CH_2O-$, $-SCH_2-$, $-CH_2S-$, $-CH=CH-COO-$, $-OOC-CH=CH-$ or a single bond.

However, many of the compounds disclosed in these literatures do not have high helical twisting power.

CITATION LIST

Patent Literature

[Patent Literature 1] Japanese Patent Application Laid-Open (JP-A) No. H09-20781
[Patent Literature 2] JP-A No. H09-031077
[Patent Literature 3] JP-A No. H11-193287
[Patent Literature 4] JP-A No. 2000-309589
[Patent Literature 5] JP-A No. 2003-137887

SUMMARY OF INVENTION

Technical Problem

The present invention was achieved in view of the above circumstances. An object of the present invention is to provide a novel polymerizable chiral compound having high helical twisting power, a polymerizable liquid crystal composition comprising the polymerizable chiral compound, a liquid crystal polymer obtained by polymerization of the polymerizable liquid crystal composition, and an optically anisotropic body comprising the liquid crystal polymer as a constitutional material.

Solution to Problem

As a result of diligent researches, the inventors of the present invention found out that a specific polymerizable chiral compound represented by the below-described formula (I) has high helical twisting power (HTP), and they reached the present invention.

First, the present invention provides the following polymerizable chiral compounds (1) to (7).

(1) A polymerizable chiral compound represented by the following formula (I):

[Chemical formula 2]

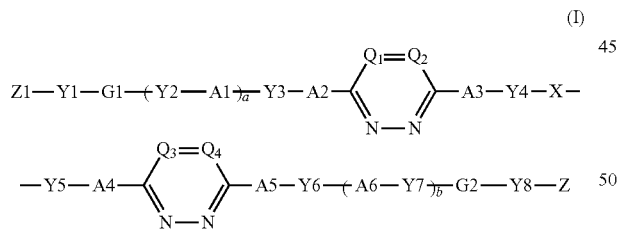

wherein Y1 to Y8 are each independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$— or —NR$^1$—O—, and R$^1$ is a hydrogen atom or an alkyl group having 1 to 6 carbon atoms;

wherein G1 and G2 are each independently a divalent aliphatic group having 1 to 20 carbon atoms, which may have a substituent; the aliphatic group may contain —O—, —S—, —O—C(=O)—, —C(=O)—O—, —O—C(=O)—O—, —NR$^2$—C(=O)—, —C(=O)—NR$^2$—, —NR$^2$— or —C(=O)— unless two or more —O— are adjacent as well as two or more —S—; R$^2$ is a hydrogen atom or an alkyl group having 1 to 6 carbon atoms; and Z1 and Z2 are each independently an alkenyl group having 2 to 10 carbon atoms, which may be substituted by a halogen atom;

wherein $Q_1$ to $Q_4$ are each independently a hydrogen atom or an alkyl group having 1 to 6 carbon atoms, which may have a substituent;

wherein A1 to A6 are each independently a divalent aromatic group A having 6 to 30 carbon atoms;

wherein X is any of groups represented by the following (X-i) to (X-vi):

[Chemical formulae 3]

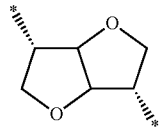
(X-i)

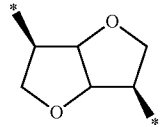
(X-ii)

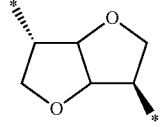
(X-iii)

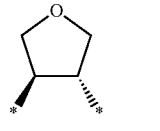
(X-iv)

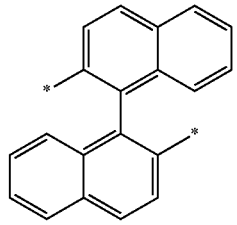
(X-v)

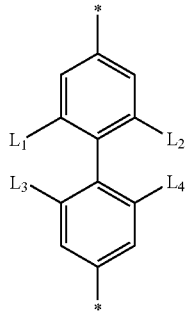
(X-vi)

wherein * represents a bond; $L_1$ to $L_4$ are each independently an alkyl group having 1 to 4 carbon atoms, an alkoxy group having 1 to 4 carbon atoms, a halogen atom, —COOR$^3$, —OCOR$^3$, —OCOOR$^3$, —CONHR$^3$ or NHCOR$^3$; and R$^3$ is a hydrogen atom or an alkyl group having 1 to 6 carbon atoms;

and wherein, in the formula (I), a and b are each independently 0 or 1.

(2) The polymerizable chiral compound according to the above (1), wherein A1 to A6 of the formula (I) are each independently a phenylene group which may have a substituent, a biphenylene group which may have a substituent, or a naphthylene group which may have a substituent.

(3) The polymerizable chiral compound according to the above (1) or (2), wherein Z1 and Z2 of the formula (I) are each independently $CH_2=CH-$, $CH_2=C(CH_3)-$, $CH_2=C(Cl)-$, $CH_2=CH-CH_2-$, $CH_2=C(CH_3)-CH_2-$, $CH_2=C(CH_3)-CH_2CH_2-$, $(CH_3)_2C=CH-CH_2-$, $CH_3-CH=CH-$ or $CH_3-CH=CH-CH_2-$.

(4) The polymerizable chiral compound according to any of the above (1) to (3), wherein X of the formula (I) is the following (X-iii):

[Chemical formula 4]

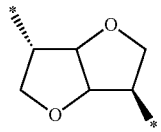

(X-iii)

wherein * represents a bond.

(5) The polymerizable chiral compound according to any of the above (1) to (4), in the formula (I), wherein Y1 to Y8 are each independently $-C(=O)-O-$, $-O-C(=O)-$ or $-O-$;

wherein G1 and G2 are each independently $-(CH_2)_6-$ or $-(CH_2)_4-$, which may contain $-O-$, $-C(=O)-O-$, $-O-C(=O)-$ or $-C(=O)-$;

wherein Z1 and Z2 are each independently $CH_2=CH-$, $CH_2=C(CH_3)-$ or $CH_2=C(Cl)-$; and wherein A1 to A6 are each independently any of groups represented by the following (A-i), (A-ii) and (A-iii):

[Chemical formula 5]

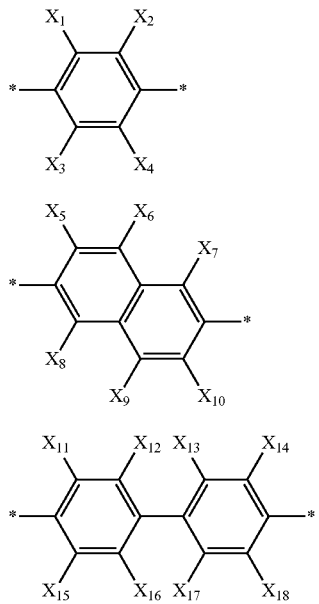

(A-i)

(A-ii)

(A-iii)

wherein * represents a bond; $X_1$ to $X_{18}$ are each independently a hydrogen atom, a halogen atom, an alkyl group having 1 to 10 carbon atoms, which may have a substituent, a cyano group, a nitro group, $-OR^4$, $-O-C(=O)-R^4$, $-C(=O)-OR^4$, $-O-C(=O)-OR^4$, $-NR^5-C(=O)-R^4$, $-C(=O)-N(R^4)R^5$ or $-O-C(=O)-N(R^4)R^5$; $R^4$ and $R^5$ are each independently a hydrogen atom or an alkyl group having 1 to 10 carbon atoms, which may have a substituent; with the provision that if $R^4$ and/or $R^5$ is an alkyl group, the alkyl group may contain $-O-$, $-S-$, $-O-C(=O)-$, $-C(=O)-O-$, $-O-C(=O)-O-$, $-NR^6-C(=O)-$, $-C(=O)-NR^6-$, $-NR^6-$ or $-C(=O)-$ unless two or more $-O-$ are adjacent as well as two or more $-S-$; and $R^6$ is a hydrogen atom or an alkyl group having 1 to 6 carbon atoms.

(6) The polymerizable chiral compound according to any of the above (1) to (5), in the formula (I), wherein Y1 to Y8 are each independently $-C(=O)-O-$, $-O-C(=O)-$ or $-O-$;

wherein G1 and G2 are each independently $-(CH_2)_6-$ or $-(CH_2)_4-$;

wherein Z1 and Z2 are each independently $CH_2=CH-$ or $CH_2=C(CH_3)-$; and wherein A1 to A6 are each independently a group represented by the following (A-i):

[Chemical formula 6]

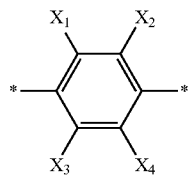

(A-i)

wherein * represents a bond; X1 to X4 are each independently a hydrogen atom, a halogen atom, an alkyl group having 1 to 10 carbon atoms, which may have a substituent, a cyano group, a nitro group, $-OR^4$, $-O-C(=O)-R^4$, $-C(=O)-OR^4$, $-O-C(=O)-OR^4$, $-NR^5-C(=O)-R^4$, $-C(=O)-N(R^4)R^5$ or $-O-C(=O)-N(R^4)R^5$; $R^4$ and $R^5$ are each independently a hydrogen atom or an alkyl group having 1 to 10 carbon atoms, which may have a substituent; with the provision that if $R^4$ and/or $R^5$ is an alkyl group, the alkyl group may contain $-O-$, $-S-$, $-O-C(=O)-$, $-C(=O)-O-$, $-O-C(=O)-O-$, $-NR^6-C(=O)-$, $-C(=O)-NR^6-$, $-NR^6-$ or $C(=O)-$ unless two or more $-O-$ are adjacent as well as two or more $-S-$; and $R^6$ is a hydrogen atom or an alkyl group having 1 to 6 carbon atoms.

(7) The polymerizable chiral compound according to any of the above (1) to (6), in the formula (I), wherein Y1 to Y8 are each independently $-C(=O)-O-$, $-O-C(=O)-$ or $-O-$;

wherein G1 and G2 are each independently $-(CH_2)_6-$ or $-(CH_2)_4-$;

wherein Z1 and Z2 are $CH_2=CH-$;

wherein $Q_1$ to $Q_4$ are each independently a hydrogen atom or a methyl group; and wherein A1 to A6 are each independently a group represented by the following (A-i):

[Chemical formula 7]

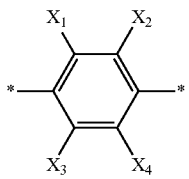

(A-i)

wherein * represents a bond; $X_1$ to $X_4$ are each independently a hydrogen atom, a halogen atom, an alkyl group having 1 to 10 carbon atoms, which may have a substituent, a cyano group, a nitro group, —$OR^4$, —O—C(═O)—$R^4$ or —C(═O)—$OR^4$; $R^4$ is a hydrogen atom or an alkyl group having 1 to 10 carbon atoms, which may have a substituent; and with the provision that if $R^4$ is an alkyl group, the alkyl group may contain —O—, —S—, —O—C(═O)—, —C(═O)—O— or C(═O)— unless two or more —O— are adjacent as well as two or more —S—.

The second invention of the present invention provides a polymerizable liquid crystal composition in the following (8).

(8) A polymerizable liquid crystal composition comprising the polymerizable chiral compound defined by any of the above (1) to (7) and a polymerizable liquid crystal compound.

The third invention of the present invention provides a liquid crystal polymer in the following (9).

(9) A liquid crystal polymer obtained by polymerization of the polymerizable liquid crystal composition defined by the above (8).

The fourth invention of the present invention provides an optically anisotropic substance in the following (10).

(10) An optically anisotropic body comprising the liquid crystal polymer defined by the above (9) as a constitutional material.

Advantageous Effects of Invention

The present invention provides a novel polymerizable chiral compound having high helical twisting power, a polymerizable liquid crystal composition comprising the polymerizable chiral compound, a liquid crystal polymer obtained by polymerization of the polymerizable liquid crystal composition, and an optically anisotropic body comprising the liquid crystal polymer as a constitutional material.

DESCRIPTION OF EMBODIMENTS

Hereinafter, the present invention will be divided into 1) polymerizable chiral compound, 2) polymerizable liquid crystal composition, 3) liquid crystal polymer and 4) optically anisotropic body, and will be described in detail.

1) Polymerizable Chiral Compound

The polymerizable chiral compound of the present invention is a compound represented by the formula (I).

In the formula (I), Y1 to Y8 are each independently a chemical single bond, —O—, —S—, —O—C(═O)—, —C(═O)—O—, —O—C(═O)—O—, —$NR^1$—C(═O)—, —C(═O)—$NR^1$—, —O—C(═O)—$NR^1$—, —$NR^1$—C(═O)—O—, —$NR^1$—C(═O)—$NR^1$—, —O—$NR^1$— or —$NR^1$—O—.

Among them, —O—, —O—C(═O)—, and —C(═O)—O— are preferable.

$R^1$ is a hydrogen atom or an alkyl group having 1 to 6 carbon atoms such as a methyl group, an ethyl group, an n-propyl group, an isopropyl group, an n-butyl group, an isobutyl group, a sec-butyl group, a t-butyl group, an n-pentyl group, an isopentyl group, a neopentyl group and an n-hexyl group. Among them, $R^1$ is preferably a hydrogen atom or a methyl group.

G1 and G2 are each independently a divalent aliphatic group having 1 to 20 carbon atoms, which may have a substituent. Preferably, it is a divalent aliphatic group having 1 to 12 carbon atoms, which may have a substituent.

Examples of the divalent aliphatic group having 1 to 20 carbon atoms as G1 and G2 include a divalent aliphatic group having 1 to 20 carbon atoms and having a chain aliphatic group and/or an alicyclic structure. Among them, from the viewpoint of exerting the desired effects of the present invention more effectively, preferred are chain aliphatic groups such as an alkylene group having 1 to 20 carbon atoms and an alkenylene group having 2 to 20 carbon atoms. More preferred are alkylene groups having 1 to 12 carbon atoms such as a methylene group, an ethylene group, a trimethylene group, a propylene group, a tetramethylene group, a pentamethylene group, a hexamethylene group and an octamethylene group. Particularly preferred are a tetramethylene group (—$(CH_2)_4$—) and a hexamethylene group (—$(CH_2)_6$—).

Examples of the substituent of the aliphatic group as G1 and G2 include halogen atoms such as a fluorine atom, a chlorine atom, a bromine atom and an iodine atom, and alkoxy groups having 1 to 6 carbon atoms such as a methoxy group, an ethoxy group, an n-propoxy group, an isopropoxy group, an n-butoxy group, a sec-butoxy group, a t-butoxy group, an n-pentyloxy group and a n-hexyloxy group. Among them, preferred are a fluorine atom, a methoxy group and an ethoxy group.

The aliphatic group may contain —O—, —S—, —O—C(═O)—, —C(═O)—O—, —O—C(═O)—O—, —$NR^2$—C(═O)—, —C(═O)—$NR^2$—, —$NR^2$— or —C(═O)— unless two or more —O— are adjacent as well as two or more —S—. Among the above, —O—, —O—C(═O)—, —C(═O)—O— and —C(═O)— are preferred.

As with $R^1$, $R^2$ is a hydrogen atom or an alkyl group having 1 to 6 carbon atoms. $R^2$ is preferably a hydrogen atom or a methyl group.

Specific examples of the aliphatic group containing the above groups include —$CH_2$—$CH_2$—O—$CH_2$—$CH_2$—, —$CH_2$—$CH_2$—S—$CH_2$—$CH_2$—, —$CH_2$—$CH_2$—O—C(═O)—$CH_2$—$CH_2$—, —$CH_2$—$CH_2$—C(═O)—O—$CH_2$—, —$CH_2$—$CH_2$—C(═O)—O—$CH_2$—$CH_2$—, —$CH_2$—$CH_2$—$NR^2$—C(═O)— —$CH_2$—$CH_2$—, —$CH_2$—$CH_2$—C(═O)—$NR^2$—$CH_2$—, —$CH_2$—$NR^2$—$CH_2$—$CH_2$— and —$CH_2$—C(═O) —$CH_2$—.

Z1 and Z2 are each independently an alkenyl group having 2 to 10 carbon atoms, which may be substituted by a halogen atom.

The alkenyl group having 2 to 10 carbon atoms as Z1 and Z2, which may be substituted by a halogen atom, is preferably an alkenyl group having 2 to 6 carbon atoms. Examples of the halogen atom (substituent) include a fluorine atom, a chlorine atom and bromine atom, and preferred is a chlorine atom.

Specific examples of the alkenyl group having 2 to 10 carbon atoms as Z1 and Z2, which may be substituted by a halogen atom, include $CH_2$═CH—, $CH_2$═C($CH_3$)—, $CH_2$═CH—$CH_2$—, $CH_3$—CH═CH—, $CH_2$═CH—$CH_2$—$CH_2$—, $CH_2$═C($CH_3$)—$CH_2$—$CH_2$—, $(CH_3)_2$C═CH—$CH_2$—, $(CH_3)_2$C═CH—$CH_2$—$CH_2$—, $CH_2$═C(Cl)—, $CH_2$═C($CH_3$)—$CH_2$— and $CH_3$—CH═CH—$CH_2$—.

Among them, from the viewpoint of exerting the desired effects of the present invention more effectively, preferred are $CH_2=CH-$, $CH_2=C(CH_3)-$, $CH_2=C(Cl)-$, $CH_2=CH-CH_2-$, $CH_2=C(CH_3)-CH_2-$ and $CH_2=C(CH_3)-CH_2-CH_2-$. More preferred are $CH_2=CH-$, $CH_2=C(CH_3)-$ and $CH_2=C(Cl)-$, and still more preferred are $CH_2=CH-$ and $CH_2=C(CH_3)-$. Particularly preferred is $CH_2=CH-$.

Q1 to Q4 are each independently a hydrogen atom or, as with $R^1$, an alkyl group having 1 to 6 carbon atoms, which may have a substituent. Among them, preferably, Q1 to Q4 are each independently a hydrogen atom or methyl group, and more preferably a hydrogen atom.

A1 to A6 are each independently a divalent aromatic group A having 6 to 30 carbon atoms.

Examples of the divalent aromatic group include divalent hydrocarbon groups containing a monocyclic aromatic hydrocarbon having one benzene ring, such as benzene, toluene and xylene, and divalent hydrocarbon groups containing a polycyclic aromatic hydrocarbon having two or more (generally two to four) benzene rings, such as naphthalene, biphenyl and terphenyl.

Among them, preferably, A1 to A6 are each independently a phenylene group which may have a substituent, a biphenylene group which may have a substituent, or a naphthylene group which may have a substituent. More preferably, A1 to A6 are each independently any of groups represented by the following (A-i), (A-ii) and (A-iii), and particularly preferably a group represented by (A-i):

[Chemical formulae 8]

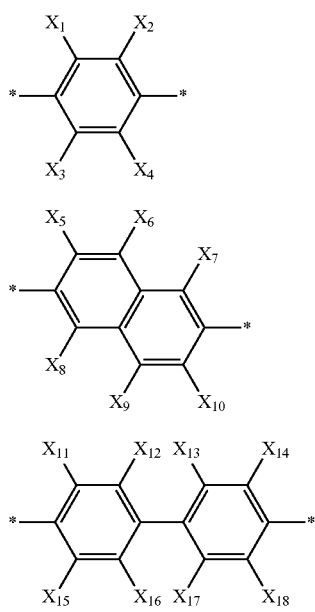

wherein * represents a bond; $X_1$ to $X_{18}$ are each independently a hydrogen atom, a halogen atom, an alkyl group having 1 to 10 carbon atoms, which may have a substituent, a cyano group, a nitro group, $-OR^4$, $-O-C(=O)-R^4$, $-C(=O)-OR^4$, $-O-C(=O)-OR^4$, $-NR^5-C(=O)-R^4$, $-C(=O)-N(R^4)R^5$ or $-O-C(=O)-N(R^4)R^5$.

$R^4$ and $R^5$ are each independently a hydrogen atom or an alkyl group having 1 to 10 carbon atoms, which may have a substituent.

Examples of the alkyl group having 1 to 10 carbon atoms as $R^4$ and $R^5$, which may have a substituent, include a methyl group, an ethyl group, an n-propyl group, an isopropyl group, an n-butyl group, an s-butyl group, an isobutyl group, a t-butyl group, an n-pentyl group, an n-hexyl group, an n-heptyl group, an n-octyl group, an n-nonyl group and an n-decyl group. Preferred are a methyl group, an ethyl group, an n-propyl group and an isopropyl group.

Examples of the substituent of the alkyl group having 1 to 10 carbon atoms, which may have a substituent, include halogen atoms such as a fluorine atom, a chlorine atom, a bromine atom and an iodine atom, and alkoxy groups having 1 to 6 carbon atoms such as a methoxy group, an ethoxy group, an n-propoxy group, an isopropoxy group, an n-butoxy group, a sec-butoxy group, a t-butoxy group, an n-pentyloxy group and an n-hexyloxy group.

If $R^4$ and/or $R^5$ is an alkyl group, the alkyl group may contain $-O-$, $-S-$, $-O-C(=O)-$, $C(=O)-O-$, $-O-C(=O)-O-$, $-NR^6-C(=O)-$, $-C(=O)-NR^6-$, $-NR^6-$ or $-C(=O)-$ unless two or more $-O-$ are adjacent as well as two or more $-S-$.

$R^6$ is a hydrogen atom or, as with $R^1$, an alkyl group having 1 to 6 carbon atoms.

X is any of groups represented by the following (X-i) to (X-vi). Preferred are (X-i) to (x-iii), and particularly preferred is (X-iii).

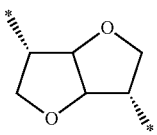

(X-i)

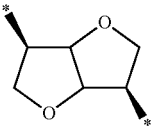

(X-ii)

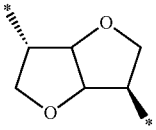

(X-iii)

(X-iv)

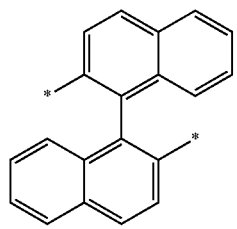

(X-v)

(X-vi)

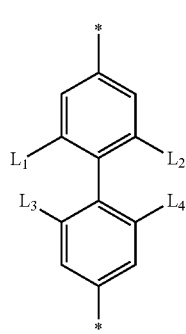

In the formulae (X-i) to (X-vi), * represents a bond.

$L_1$ to $L_4$ are each independently an alkyl group having 1 to 4 carbon atoms such as a methyl group or ethyl group, an alkoxy group having 1 to 4 carbon atoms such as a methoxy group or ethoxy group, a halogen atom such as a fluorine atom, chlorine atom or bromine atom, —COOR$^3$, —OCOR$^3$, —OCOOR$^3$, —CONHR$^3$ or NHCOR$^3$.

$R^3$ is a hydrogen atom or, as with $R^1$, an alkyl group having 1 to 6 carbon atoms.

In the formula (I), a and b are each independently 0 or 1. From the viewpoint of ease of synthesis, both of a and b are preferably 0 or 1. Furthermore, from the viewpoint of helical twisting power, both of a and b are more preferably 1.

The polymerizable chiral compound of the present invention is preferably the following (α), more preferably the following (β), still more preferably the following (γ).

(α) A compound wherein, in the formula (I), Y1 to Y8 are each independently —C(=O)—O—, —O—C(=O)— or —O—; G1 and G2 are each independently —(CH$_2$)$_6$— or —(CH$_2$)$_4$—, which may contain —O—, —C(=O)—O—, —O—C(=O)— or —C(=O)—; Z1 and Z2 are each independently CH$_2$=CH—, CH$_2$=C(CH$_3$)— or CH$_2$=C(Cl)—; and A1 to A6 are each independently any of groups represented by the (A-i), (A-ii) and (A-iii).

(β) A compound wherein, in the formula (I), Y1 to Y8 are each independently —C(=O)—O—, —O—C(=O)— or —O—; G1 and G2 are each independently —(CH$_2$)$_6$— or —(CH$_2$)$_4$—; Z1 and Z2 are each independently CH$_2$=CH— or CH$_2$=C(CH$_3$)—; and A1 to A6 are each independently a group represented by (A-i).

(γ) A compound wherein, in the formula (I), Y1 to Y8 are each independently —C(=O)—O—, —O—C(=O)— or —O—; G1 and G2 are each independently —(CH$_2$)$_6$— or —(CH$_2$)$_4$—; Z1 and Z2 are CH$_2$=CH—; Q1 and Q2 are each independently a hydrogen atom or a methyl group; and A1 to A6 are each independently a group represented by (A-i).

1-a) Production of Polymerizable Chiral Compound

Any of the polymerizable chiral compounds of the present invention can be produced by a combination of known methods for forming various kinds of chemical bonds such as —O—, —S—, —NH—C(=O)—, —C(=O)—NH—, —NH—C(=O)—NH—, —O—C(=O)— and —C(=O)—O— (for example, see: Sandler & Karo, Syntheses of Organic compounds Classified by Functional Group, Vol. I and Vol. II, Hirokawa Shoten, Tokyo (1976)).

Typically, the polymerizable chiral compound of the present invention can be produced by appropriately bonding/modifying known compounds with desired structures by optionally combining an ether bond (—O—)-forming reaction, an ester bond (—C(=O)—O—)-forming reaction, an amide bond (—C(=O)NH—)-forming reaction and an acid chloride (—COCl)-forming reaction.

An ether bond can be formed by the following methods, for example.

(i) A compound represented by the formula D1-hal (hal represents a halogen atom, and this is the same in the following methods) and a compound represented by the formula D2-OMet (Met represents an alkali metal (mainly sodium) and this is the same in the following methods) are mixed and condensed. In these formulae, each of D1 and D2 represents an optional organic group B (this is the same in the following methods). This reaction is generally called the Williamson synthesis.

(ii) A compound represented by the formula D1-hal and a compound represented by the formula D2-OH are mixed and condensed in the presence of a base such as sodium hydroxide or potassium hydroxide.

(iii) A compound represented by the formula D1-E (E represents an epoxy group) and a compound represented by the formula D2-OH are mixed and condensed in the presence of a base such as sodium hydroxide or potassium hydroxide.

(iv) A compound represented by the formula D1-OFN (OFN represents a group having an unsaturated bond) and a compound represented by the formula D2-OMet are mixed to initiate an addition reaction in the presence of a base such as sodium hydroxide or potassium hydroxide.

(v) A compound represented by the formula D1-hal and a compound represented by the formula D2-OMet are mixed and condensed in the presence of copper or copper (I) chloride. This reaction is generally called the Ullmann condensation.

Ester bond and amide bond can be carried out by the following methods, for example.

(vi) A compound represented by the formula D1-COOH and a compound represented by the formula D2-OH or D2-NH$_2$ are subjected to dehydration condensation in the presence of a dehydration-condensation agent (e.g., N,N-dicyclohexylcarbodiimide).

(vii) A compound represented by the formula D1-CO-hal is obtained by the action of a halogenating agent on a compound represented by the formula D1-COOH. The thus-obtained compound and a compound represented by the formula D2-OH or D2-NH$_2$ are reacted in the presence of a base.

(viii) A mixed acid anhydride is obtained by the action of an acid anhydride on a compound represented by the formula D1-COOH. The thus-obtained mixed acid anhydride is reacted with a compound represented by the formula D2-OH or D2-NH$_2$.

(ix) A compound represented by the formula D1-COOH and a compound represented by the formula D2-OH or D2-NH$_2$ are subjected to dehydration condensation in the presence of an acid catalyst or base catalyst.

Acid chloride formation can be carried out by the following methods, for example.

(x) By the action of phosphorous trichloride or phosphorous pentachloride on a compound represented by the formula D1-COOH.

(xi) By the action of thionyl chloride on a compound represented by the formula D1-COON.

(xii) By the action of oxalyl chloride on a compound represented by the formula D1-COOH.

(xiii) By the action of chlorine on a compound represented by the formula D1-COOAg (Ag: silver).

(xiv) By the action of a carbon tetrachloride solution of red mercury(II) oxide on a compound represented by the formula D1-COOH.

In the production of the polymerizable chiral compound of the present invention (particularly in the production of a polymerizable chiral compound having an asymmetric structure), it is sometimes possible to facilitate the synthesis by protecting a hydroxyl group that is present in an intermediate, and thus the yield can be increased.

There are known methods that can be used to protect the hydroxyl group (for example, see Greene's Protective Groups in Organic Synthesis, $3^{rd}$ edition, published by Wiley-Interscience (1999)).

The hydroxyl group can be protected by the following methods, for example.

(xv) A compound represented by the formula D1D2D3-Si-hal is mixed and reacted with a compound represented by the formula D4-OH in the presence of a base such as imidazole or pyridine. In the formulae, each of D3 and D4 represents an optional organic group B (this is the same in the following methods).

(xvi) A vinyl ether such as 3,4-dihydro-2H-pyran is mixed and reacted with a compound represented by the formula D2-OH in the presence of an acid such as p-toluenesulfonic acid, pyridinium p-toluenesulfonate or hydrogen chloride.

(xvii) A compound represented by the formula D1-C(=O)-hal is mixed and reacted with a compound represented by the formula D4-OH in the presence of a base such as triethylamine or pyridine.

(xviii) An acid anhydride represented by the formula D1-C(=O)—O—C(=O)-D2 is mixed and reacted with a compound represented by the formula D3-OH, or they are mixed and reacted in the presence of a base such as sodium hydroxide or triethylamine.

(xix) A compound represented by the formula D1-hal is mixed and reacted with a compound represented by the formula D2-OH in the presence of a base such as sodium hydroxide or triethylamine.

(xx) A compound represented by the formula D1-O—CH$_2$-hal is mixed and reacted with a compound represented by the formula D2-OH in the presence of a base such as sodium hydride, sodium hydroxide, triethylamine or pyridine.

(xxi) A compound represented by the formula D1-O—CH$_2$—C(=O)-hal is mixed and reacted with a compound represented by the formula D2-OH in the presence of a base such as potassium carbonate or sodium hydroxide.

(xxii) A compound represented by the formula D1-O—C(=O)-hal is mixed and reacted with a compound represented by the formula D2-OH in the presence of a base such as triethylamine or pyridine.

Deprotection can be performed by the following known methods, depending on the structure and type of the protecting group.

(xxiii) By mixing with a fluorine ion such as tetrabutylammonium fluoride.

(xxiv) By mixing in the presence of an acid such as p-toluenesulfonic acid, pyridinium p-toluenesulfonate, hydrogen chloride or acetic acid.

(xxv) By mixing in the presence of a base such as sodium hydride, sodium hydroxide, potassium hydroxide, sodium carbonate, potassium carbonate, triethylamine or pyridine.

(xxvi) By hydrogenation in the presence of a catalyst such as Pd—C.

In particular, the polymerizable chiral compound of the present invention can be obtained as follows, for example.

[Chemical formula 9]

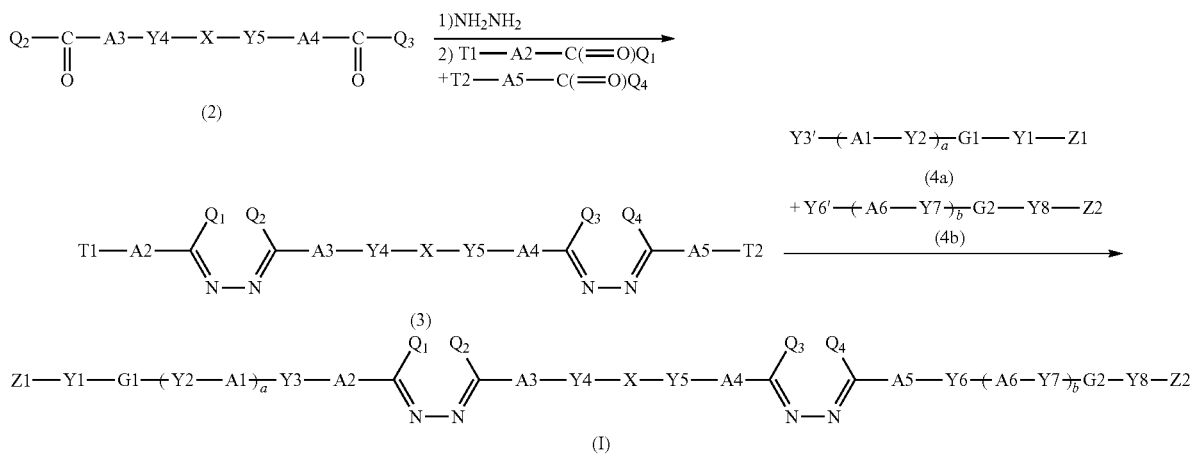

wherein each of A1 to A6, X, Y1 to Y8, $Q_1$ to $Q_4$, G1, G2, Z1, Z2, a and b represents the same meaning as above; T1 represents a group that reacts with Y3' to produce Y3; and T2 represents a group that reacts with Y6' to produce Y6. For example, in the case where T1 and T2 are each a hydroxyl group (OH) and Y3' and Y6' are each a carboxyl group (COOH), T1 and T2 react with Y3' and Y6', respectively, to produce Y3 [—C(=O)—O—] and Y6 [—O—C(=O)—], respectively.

In particular, the compound represented by the formula (2) is reacted with hydrazine (or hydrazine monohydrate) and then with the compounds represented by the formulae T1-A2-O(=O)Q1 and T2-A5-C(=O)Q$_4$ to obtain an intermediate represented by the formula (3) (step 1). Next, the thus-obtained intermediate is reacted with compounds represented by the formulae (4a) and (4b) (step 2), thereby obtaining the target compound represented by the formula (I) (the polymerizable chiral compound of the present invention).

The step 1 can be carried out in an appropriate organic solvent.

Examples of the organic solvent to be used include alcohol solvents such as methanol, ethanol, n-propanol, isopropanol and n-butanol; ether solvents such as diethyl ether, tetrahydrofuran, 1,2-dimethoxyethane and 1,4-dioxane; ester solvents such as ethyl acetate, propyl acetate and methyl propionate; aromatic hydrocarbon solvents such as benzene, toluene and xylene; aliphatic hydrocarbon solvents such as n-pentane, n-hexane and n-heptane; amide solvents such as N,N-dimethylformamide, N-methylpyrrolidone and hexamethylphosphoric triamide; sulfur-containing solvents such as dimethylsulfoxide and sulfolane; and mixed solvents comprising two or more of the above solvents.

In the step 1, the used amount of hydrazine is generally 2 to 10 times the amount of the compound represented by the formula (2) in a molar ratio.

The used amount of the compounds represented by the formulae T1-A2-C(=O) $Q_1$ and T2-A5-C(=O) $Q_4$ are generally 0.5 to 5 times the amount of the compound represented by the formula (2) in a molar ratio. If the compounds represented by the formulae T1-A2-C(=O)$Q_1$ and T2-A5-C(=O)$Q_4$ are identical, they can be used in an amount that is two or more times the amount of the compound represented by the formula (2) in a molar ratio.

The reaction in the step 1 proceeds smoothly in the temperature range of −10° C. to the boiling point of the solvent.

The reaction time depends on the reaction scale but is generally several minutes to several hours.

A reaction solution containing the compound represented by the formula (3) is obtained in the manner as described above.

In the present invention, the compound represented by the formula (3) can be separated from the reaction solution and used in the next step 2, or the reaction solution containing the compound represented by the formula (3) can be used as it is in the step 2, without separating the compound represented by the formula (3).

The compound represented by the formula (3) can be also produced by the following method.

[Chemical formula 10]

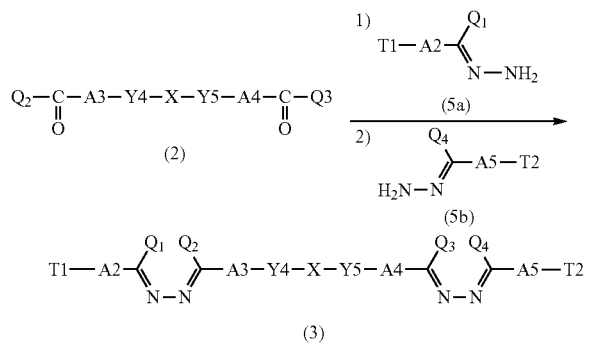

wherein each of A2 to A5, X, Y4, Y5, $Q_1$ to $Q_4$, T1 and T2 represents the same meaning as above.

In particular, the compound represented by the formula (2) is reacted with the compound represented by the formula (5a) and then with the compound represented by the formula (5b) consecutively, thereby obtaining the compound represented by the formula (3).

The compounds represented by the formulae (5a) and (5b) can be produced by the reaction of hydrazine with the compounds represented by the formulae T1-A2-C(=O)$Q_1$ and T2-A5-C(=O)$Q_4$, respectively.

Next, the compound represented by the formula (3) is reacted with the compounds represented by the formulae (4a) and (4b) (step 2), thereby obtaining the target compound represented by the formula (I) (the polymerizable chiral compound of the present invention).

Preferred specific examples of the compounds represented by the formulae (4a) and (4b) include the following compounds. The present invention is not limited to the following compounds, however.

[Chemical formulae 11]

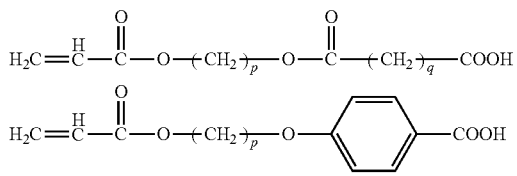

wherein, p and q are each independently an integer of 1 to 6.

The step 2 can be carried out in an appropriate organic solvent.

Examples of the organic solvent include organic solvents that are the same as those listed in the step 1.

In the step 2, the used amount of the compounds represented by the formulae (4a) and (4b) are generally 1 to 3 times the amount of the compound represented by the formula (3) in a molar ratio.

If the compounds represented by the formulae (4a) and (4b) are identical, they can be used in an amount that is two or more times the amount of the compound represented by the formula (3) in a molar ratio.

The reaction in the step 2 proceeds smoothly in the temperature range of −10° C. to the boiling point of the solvent.

The reaction time depends on the reaction scale but is generally several minutes to several hours.

A posttreatment which is usual in synthetic organic chemistry is performed after the reaction, and as needed, a known separation/purification process such as column chromatography, recrystallization method or distillation is performed, thereby separating the target compound.

The structure of the target compound can be identified by NMR spectrum measurement, IR spectrum measurement, mass spectrum measurement or elemental analysis.

The compound represented by the formula (2), which is a starting material, can be produced as follows:

[Chemical formula 12]

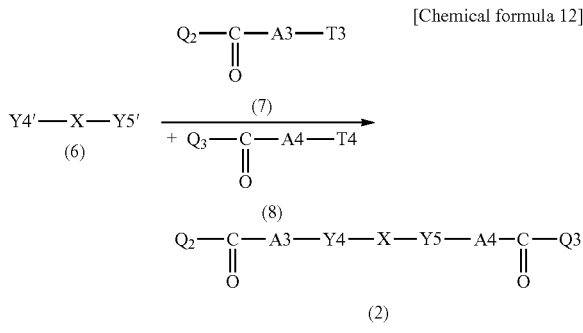

wherein each of A3, A4, X, Y4, Y5, $Q_2$ and $Q_3$ represents the same meaning as above; T3 represents a group that reacts with Y4' to produce Y4; and T4 represents a group that reacts with Y5' to produce Y5.

In particular, the compound represented by the formula (6), which will be a chiral group, is reacted with the compounds represented by the formulae (7) and (8), thereby obtaining the target compound represented by the formula (2).

Preferred specific examples of the compound represented by the formula (6) include the following compounds. The present invention is not limited to the following compounds, however.

[Chemical formulae 13]

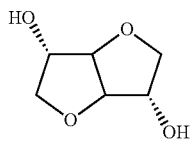

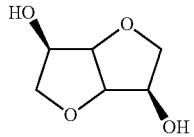

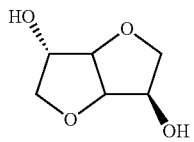

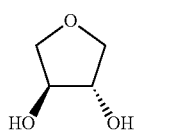

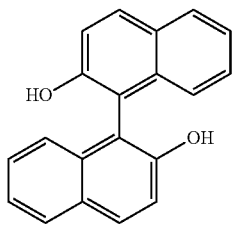

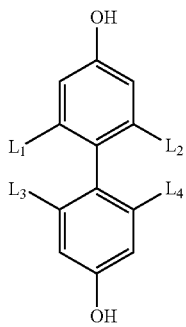

wherein each of $L_1$ to $L_4$ represents the same meaning as above.

Preferred specific examples of the compounds represented by the formulae (7) and (8) include the following compounds. The present invention is not limited to the following compounds, however.

[Chemical formulae 14]

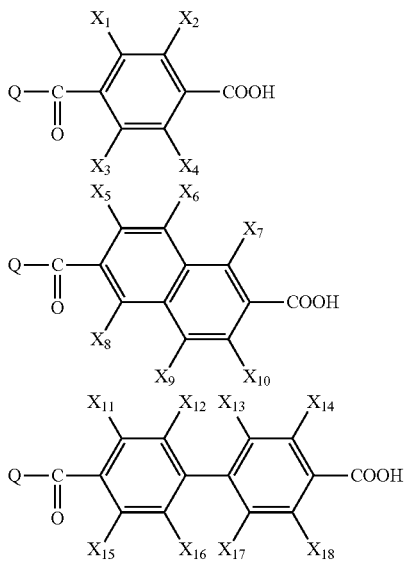

wherein each of $X_1$ to $X_{18}$ represents the same meaning as above; and Q is $Q_2$ or $Q_3$.

Many of the above compounds are known substances and can be produced by known methods.

2) Polymerizable Liquid Crystal Composition

The polymerizable liquid crystal composition of the present invention comprises at least one of the polymerizable chiral compounds of the present invention and at least one polymerizable liquid crystal compound.

The polymerizable liquid crystal compound comprising the polymerizable liquid crystal composition of the present invention exhibit a cholesteric phase when mixed with the polymerizable chiral compound of the present invention.

Specific examples of the polymerizable liquid crystal compound used for the composition of the present invention include compounds disclosed in Japanese Patent Application Laid-Open (JP-A) No. H11-130729, JP-A No. H08-104870, JP-A No. 2005-309255, JP-A No. 2005-263789, Japanese translation of PCT international application No. 2002-533742, JP-A No. 2002-308832, JP-A No. 2002-265421, JP-A No. S62-070406, JP-A No. H11-100575, PCT/JP2008/057896 and Japanese Patent Application Nos. 2008-92093, 2008-92162 and 2008-170835.

The composition of the present invention comprises one or more of the above-mentioned polymerizable liquid crystal compounds as an essential component.

In the polymerizable liquid crystal composition of the present invention, the compounding ratio of the polymerizable chiral compound is generally 0.1 to 100 parts by weight, preferably 0.5 to 10 parts by weight, more preferably 1 to 8 parts by weight, with respect to 100 parts by weight of the polymerizable liquid crystal compound.

In general, from the viewpoint of efficient polymerization reaction, the polymerizable liquid crystal composition of the present invention preferably comprises a polymerization initiator.

As the polymerization initiator, an appropriate polymerization initiator can be selected for use, according to the type of a polymerizable group that is present in the polymerizable liquid crystal compound. For example, when the polymerizable group is a radically polymerizable group, a radical polymerization initiator can be used. When the polymerizable group is an anionically polymerizable group, an anionic polymerization initiator can be used. When the polymerizable group is a cationically polymerizable group, a cationic polymerization initiator can be used.

As the radical polymerization initiator, a thermal radical generator or photo radical generator can be used. Suitably used is a photo radical generator.

Examples of the photo radical generator include benzoins such as benzoin, benzoin methyl ether and benzoin propyl ether; acetophenones such as acetophenone, 2,2-dimethoxy-2-phenylacetophenone, 2,2-diethoxy-2-phenylacetophenone, 1,1-dichloroacetophenone, 1-hydroxycyclohexylphenylketone, 2-methyl-1-[4-(methylthio)phenyl]-2-morpholino-propane-1-on and N,N-dimethylaminoacetophenone; anthraquinones such as 2-methylanthraquinone, 1-chloroanthraquinone and 2-amylanthraquinone; thioxanthones such as 2,4-dimethylthioxanthone, 2,4-diethylthioxanthone, 2-chlorothioxanthone and 2,4-diisopropylthioxanthone; ketals such as acetophenone dimethyl ketal and benzyl dimethyl ketal; benzophenones such as benzophenone, methylbenzophenone, 4,4-dichlorobenzophenone, 4,4-bisdiethylaminobenzophenone, Michler's ketone and 4-benzoyl-4-methyldiphenylsulfide; and 2,4,6-trimethylbenzoyldiphenylphosphineoxide.

Specific examples of the photo radical polymerization initiator include Irgacure 907, Irgacure 184, Irgacure 369, and Irgacure 651 (product names; manufactured by Chiba Specialty Chemicals, Inc.)

Examples of the anionic polymerization initiator include alkyllithium compounds; monolithium salts such as lithium biphenylide, lithium naphtalenide and lithium pyrenide; monosodium salts such as sodium biphenylide, sodium naphtalenide and sodium pyrenide; and multifunctional initiators such as dilithium salt or trilithium salt.

Examples of the cationic polymerization initiator include protonic acids such as sulfuric acid, phosphoric acid, perchloric acid and trifluoromethanesulfonic acid; Lewis acids such as boron trifluoride, aluminum chloride, titanium tetrachloride and tin tetrachloride; and aromatic onium salts and combinations of aromatic onium salts with a reducing agent.

These polymerization initiators can be used alone or in combination of two or more kinds.

In the polymerizable liquid crystal composition of the present invention, the compounding ratio of the polymerization initiator is generally 0.1 to 30 parts by weight, preferably 0.5 to 10 parts by weight, with respect to 100 parts by weight of the polymerizable liquid crystal compound.

When initiating the (co) polymerization of the polymerizable liquid crystal compound (with other copolymerizable monomer or the like which is used as needed), a functional compound such as an ultraviolet absorbing agent, an infrared absorbing agent or an antioxidant can be used as needed.

The polymerizable liquid crystal composition of the present invention preferably comprises a surfactant to control surface tension. The surfactant is not particularly limited, and in general, it is preferably a nonionic surfactant. As the nonionic surfactant, commercial products can be used. An example is a nonionic surfactant which is an oligomer having a molecular weight of a few thousand, such as KH-40 (product name; manufactured by: AGC SEIMI Chemical Co., Ltd.) In the polymerizable liquid crystal composition of the present invention, the compounding ratio of the surfactant is generally 0.01 to 10 parts by weight, preferably 0.1 to 2 parts by weight, with respect to 100 parts by weight of the polymerizable liquid crystal compound.

To use the polymerizable liquid crystal composition of the present invention as a material for polarizing films or alignment films, or as a printing ink, a coating material, a protecting film, etc., other additive(s) can be contained depending on the purpose in addition to the above components, such as other copolymerizable monomers mentioned below, a metal, a metal complex, a dye, a pigment, a fluorescent material, a phosphorescent material, a leveling agent, a thixotropic agent, a gelation agent, a polysaccharide, an ultraviolet absorbing agent, an infrared absorbing agent, an antioxidant, an ion-exchange resin, a metal oxide such as titanium oxide. In the polymerizable liquid crystal composition of the present invention, the compounding ratio of other additive(s) is generally 0.1 to 20 parts by weight, with respect to 100 parts by weight of the polymerizable liquid crystal compound.

In general, the polymerizable liquid crystal composition of the present invention can be prepared by dissolving, in an appropriate organic solvent, a polymerizable liquid crystal compound, the polymerizable chiral compound of the present invention, a photo polymerization initiator, a nonionic surfactant and, as needed, other additive(s), each of which is in a predetermined amount.

Examples of the organic solvent include ketones such as cyclopentanone, cyclohexanone and methyl ethyl ketone; ester acetates such as butyl acetate and amyl acetate; halogenated hydrocarbons such as chloroform, dichloromethane and dichloroethane; and ethers such as 1,2-dimethoxyethane, 1,4-dioxane, cyclopentyl methyl ether, tetrahydrofuran and tetrahydropyran.

The polymerizable liquid crystal composition obtained in the manner as described above is, as discussed in more detail below, useful as a material for producing a cholesteric liquid crystal layer and a cholesteric liquid crystal polymer.

3) Liquid Crystal Polymer

The liquid crystal polymer of the present invention is a polymer obtained by (co)polymerization of the polymerizable liquid crystal composition of the present invention.

Herein, "(co)polymerization" refers to a general (co)polymerization reaction and a chemical reaction in a broad sense, including a (co)crosslinking reaction.

The liquid crystal polymer of the present invention can be easily obtained by (co) polymerizing the polymerizable liquid crystal composition of the present invention in the presence of an polymerization initiator. The liquid crystal polymer thus obtained is a cholesteric liquid crystal polymer. In the present invention, from the viewpoint of efficient (co) polymerization reaction, it is preferable to use a polymerization initiator as mentioned above, especially a photo polymerization initiator. Hereinafter, embodiments of using the polymerizable liquid crystal composition of the present invention will be described.

In particular, the liquid crystal polymer of the present invention can be obtained by applying the polymerizable liquid crystal composition of the present invention to, for example, a support having an alignment function so that the applied composition is uniformly aligned in the state of retaining a cholesteric phase, the support being obtained by an alignment treatment, and then polymerizing the applied composition.

As the support, it is possible to use a substrate comprising a known and conventional material, irrespective of organic or inorganic. Examples of the material of the substrate include polycycloolefin products such as ZEONEX and ZEONOR (registered trademarks; manufactured by: ZEON Corporation), ARTON (registered trademark; manufactured by: JSR Corporation) and APEL (registered trademark; manufactured by: Mitsui Chemicals, Inc.), polyethylene terephthalate, polycarbonate, polyimide, polyamide, polymethylmethacrylate, polystyrene, polyvinyl chloride, polytetrafluoroethylene, cellulose, cellulose triacetate, polyethersulfone, silicon, glass and calcite. The form of the substrate can be a plate form or curved form. Substrates comprising the above materials can have an electrode layer, an antireflection function and/or a reflection function, as needed.

In the above method, to form a uniformly aligned state, a thin polyimide film is useful in controlling the alignment state of the polymerizable liquid crystal compound, the film being one that is used for general twisted nematic (TN) elements and super twisted nematic (STN) elements and being able to provide a pretilt angle.

In general, when the liquid crystal compound contacts with the support having an alignment function, the liquid crystal compound is aligned on the surface of the support along the direction in which the support was aligned by the alignment treatment. The method for performing the alignment treatment on the surface of the support has a large influence on whether the liquid crystal compound is aligned with the surface of the support horizontally, obliquely or vertically.

For example, when an alignment film having a slight pretilt angle is provided on the support, which is used for in plane switching (IPS) type liquid crystal display elements, a polymerizable liquid crystal layer which is almost horizontally aligned, is obtained.

When an alignment film used for TN liquid crystal display elements is provided on the support, a polymerizable liquid crystal layer having a slightly tilted alignment is obtained. When an alignment film used for STN liquid crystal display elements is used, a polymerizable liquid crystal layer having a highly tilted alignment is obtained.

When the polymerizable liquid crystal composition of the present invention is brought into contact with the support having a pretilt angle and a horizontal alignment function, an optically anisotropic body having a tilted alignment is obtained, in which the angle of the composition is uniform or varied continuously in the range from the surface of the support to around air interface, thus.

Also, a substrate on which regions in alignment directions that are different in a pattern are distributed, can be produced by, for example, a method for exposing an organic thin film having a functional group in a molecule thereof, the group being able to cause a photodimerization reaction, or an organic thin film having a photoisomerizable functional group in a molecule thereof (hereinafter, such organic films will be referred to as "photo-alignment film") to polarized or non-polarized light (photo-alignment method).

First, a support with uniform alignment is prepared by exposing a support having a photo-alignment film provided thereon to a light of a wavelength that is in the absorption band of the photo-alignment film. Then, the support is covered with a mask and exposed to a light in a different state from that of the light used in the first irradiation having the wavelength in the absorption wavelength of the photo-alignment film, such as a light in a different polarization state or a light having a different exposure angle and direction, so that only an exposed region has an alignment function that is different from that of a region subjected to the first exposure.

The polymerizable liquid crystal composition is brought into contact with the above-obtained support on which regions with alignment functions that are different in a pattern are distributed; therefore, on the support, regions which are in alignment directions that are different in a pattern corresponding to the alignment functions of the support, are distributed. When the polymerization by exposure to light is performed on the substrate in this state, a liquid crystal polymer film having an alignment pattern is obtained.

Especially by using, as the above-described support, a support having an almost horizontal alignment function on which regions which are in alignment directions that are different in a pattern are distributed, a liquid crystal polymer film that is particularly useful as a phase difference film is obtained.

Besides the above, as the method for obtaining an alignment pattern, it is possible to employ a method that uses no photo-alignment film, such as a method for rubbing an alignment film with a probe of an AFM (atomic force microscope) or a method for etching an optically anisotropic body. However, a method that uses a photo-alignment film is simple and thus preferable.

Examples of the method for applying the polymerizable liquid crystal composition of the present invention to the support include known and conventional coating methods such as bar coating, spin coating, roll coating, gravure coating, spraying coating, die coating, cap coating, and dipping. When employing such a method, to increase coatability, a known and conventional organic solvent can be added to the polymerizable liquid crystal composition of the present invention. In this case, it is possible to remove the organic solvent by natural drying, heat-drying, drying under reduced pressure, heat-drying under reduced pressure, etc., after the polymerizable liquid crystal composition of the present invention is applied to the support.

It is preferable that after the application of the composition, the liquid crystal compound in the polymerizable liquid crystal composition of the present invention is uniformly aligned in the state of retaining a cholesteric phase. In particular, the alignment can be facilitated further by performing a heating treatment that facilitates alignment of liquid crystal. The temperature of the heating treatment is generally 50 to 150° C., preferably 70 to 140° C. The time of the heating treatment is generally 0.5 to 15 minutes, preferably 2 to 10 minutes.

A desirable heat treatment method is as follows. For example, the polymerizable liquid crystal composition of the present invention is applied to the support and then heated to the C(solid phase)-N(nematic phase) transition temperature (hereinafter referred to as "C-N transition temperature") or higher of the liquid crystal composition to make the polymerizable liquid crystal composition be in a liquid crystal state or in an isotropic phase liquid state. Then, if necessary, the composition is gradually cooled to exhibit a cholesteric phase. At this stage, the composition is kept at a temperature that allows the composition to be in a liquid crystal phase, so that a liquid crystal phase domain is sufficiently developed to be a monodomain.

It is also possible that after the polymerizable liquid crystal composition of the present invention is applied to the support, a heating treatment can be performed thereon, which keeps the temperature of the composition within the temperature range that allows the composition to exhibit a cholesteric phase for a predetermined period of time.

When the heating temperature is too high, the polymerizable liquid crystal compound can cause an undesirable polymerization reaction and thus deteriorate. When the polymerizable liquid crystal composition is cooled too much, it can cause phase separation and thus exhibit precipitation of crystals or a higher liquid crystal phase such as a smectic phase; therefore, it can be impossible to perform the alignment treatment.

A liquid crystal polymer film can be produced by performing such a heating treatment, which has less alignment defects and uniform alignment compared to a coating method which consists of simply a coating step.

It is also possible to obtain a liquid crystal polymer film by, after performing the uniform alignment treatment as described above, cooling the polymerizable liquid crystal composition the lowest temperature at which the liquid crystal phase causes no phase separation, that is, into a supercooled state, and then polymerizing the composition at the same temperature in the state that the liquid crystal phase is aligned. Thereby, a liquid crystal polymer film having a better alignment order and excellent transparency is obtained.

Examples of the method for polymerizing the polymerizable liquid crystal composition include a method for applying active energy rays and a thermal polymerization method. Since no heating is required and the reaction proceeds at room temperature, the method for applying active energy rays is preferred. Due to simple operation, a method for applying light such as ultraviolet light is particularly preferable.

Upon the exposure, the temperature is set to a temperature at which the polymerizable liquid crystal composition can retain the liquid crystal phase and, if at all possible, the temperature is preferably set to 30° C. or less to prevent the polymerizable liquid crystal compound or the polymerizable liquid crystal composition from inducing thermal polymerization. In the temperature increasing process, generally the polymerizable liquid crystal compound and the polymerizable liquid crystal composition exhibit a liquid crystal phase within the range from the C-N transition temperature to the N (nematic phase)-I (isotropic liquid phase) transition temperature (hereinafter referred to as "N-I transition temperature"). On the other hand, in the temperature decreasing process, the polymerizable liquid crystal compound and the polymerizable liquid crystal composition keep a thermodynamically non-equilibrium state, so that sometimes they are not solidified even at the C-N transition temperature or less and keep a liquid crystal state. This state is called a supercooled state. In the present invention, the polymerizable liquid crystal compound and polymerizable liquid crystal compound composition in the supercooled state are considered to be in the state of retaining a liquid crystal phase. Ultraviolet irradiation intensity is generally in the range of 1 W/m² to 10 kW/m², preferably in the range of 5 W/m² to 2 kW/m².

A liquid crystal polymer film having regions in different alignment directions can be obtained by, after a specific region only is polymerized by exposure to ultraviolet light through a mask, changing the alignment state of a non-polymerized region by applying an electric or magnetic field or by heating, and then polymerizing the non-polymerized region.

A liquid crystal polymer film having regions indifferent alignment directions can be also obtained by, before a specific region only is polymerized by exposure to ultraviolet light through a mask, previously controlling the alignment of the polymerizable liquid crystal composition which is in an unpolymerized state by applying an electric or magnetic field or by heating, and then polymerizing the same kept in that state by exposure to light through a mask.

The liquid crystal polymer obtained by (co)polymerization of the polymerizable liquid crystal composition of the present invention can be used solely as an optically anisotropic body after removing the support therefrom, or it can be used as it is as an optically anisotropic body without removing the support.

Particularly, the liquid crystal polymer film obtained by (co)polymerization of the polymerizable liquid crystal composition of the present invention is a cholesteric liquid crystal film and has a significantly high reflectance, so that it is suitable as a polarizer of a liquid crystal display element.

Also, it is possible to obtain a multilayered polarizer that corresponds to all lights in the visible region of a spectrum by laminating a plurality of such a liquid crystal polymer film using a laminating method and appropriately selecting the wavelength of a liquid crystal polymer film to be selected (see EP No. 0720041).

Instead of such a multilayered polarizer, the liquid crystal polymer film can be used as a broad-band polarizer in combination with an appropriate compound and processing condition. Examples of the method for producing such a polarizer include those disclosed in WO98/08135, EP0606940, GB2312529 and WO96/02016.

It is also possible to produce a color filter by using the polymerizable liquid crystal composition of the present invention. A required wavelength can be provided appropriately to the filter by a coating method which is known for one skilled in the art.

Also, it is possible to utilize the thermal discoloration properties of cholesteric liquid crystal. The color of a cholesteric layer is changed from red, green to blue by controlling the temperature. A specific region can be polymerized at a predetermined temperature using a mask.

The liquid crystal polymer of the present invention obtained in the manner as described above preferably has a number average molecular weight of 500 to 500,000, more preferably 5,000 to 300,000. The number average molecular weight is preferably in the above range, so that high film hardness and excellent handling properties are obtained. The number average molecular weight of the liquid crystal polymer can be measured by gel permeation chromatography (GPC) using monodispersed polystyrene as a standard sample and tetrahydrofuran (THF) as an eluent.

In the liquid crystal polymer of the present invention, it is presumed that crosslinking points are uniformly present in a molecule thereof. Since the liquid crystal polymer is obtained by (co)polymerizing the polymerizable liquid crystal compound of the present invention, it has high cross-linking efficiency and excellent hardness.

The liquid crystal polymer of the present invention can be used as a constitutional material of an optically anisotropic body by utilizing its alignment properties and the anisotropy of its physical properties such as a refractive index, conductivity and susceptibility. Examples of the constitutional material include a retardation plate, an alignment film for liquid crystal display elements, a polarizing plate, a viewing angle widening plate, a color filter, a low-pass filter, a light polarization prism and various kinds of optical filters.

4) Optically Anisotropic Body

The fourth invention of the present invention is an optically anisotropic body comprising the liquid crystal polymer of the present invention as a constitutional material.

Examples of the optically anisotropic body of the present invention include a retardation plate, an alignment film for liquid crystal display elements, a polarizing plate, a viewing angle widening plate, a color filter, a low-pass filter, a light polarization prism and various kinds of optical filters.

The optically anisotropic body of the present invention comprises, as a constitutional material, the liquid crystal polymer obtained by polymerizing the polymerizable liquid crystal composition of the present invention; therefore, the optically anisotropic body of the present invention has uniform and high-quality liquid crystal alignment.

EXAMPLES

The present invention will be described further in detail with reference to examples. However, the scope of the present invention may not be limited to the following examples. Herein, "part(s)" and "%" are based on weight unless otherwise noted.

The ratio of a developing solvent (solvent ratio represented in parenthesis) used for column chromatography is a volume ratio.

Example 1

Synthesis of Polymerizable Chiral Compound (I-1)

[Chemical formula 15]

Compound (I-1)

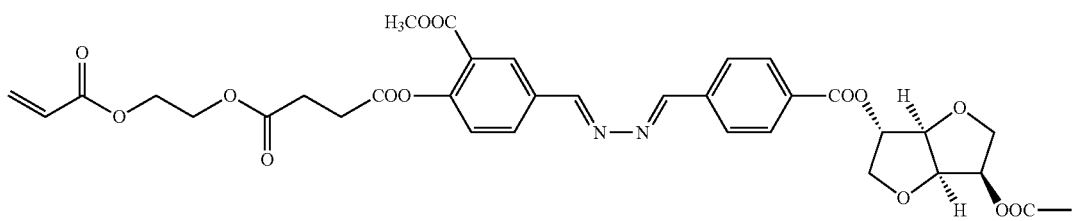

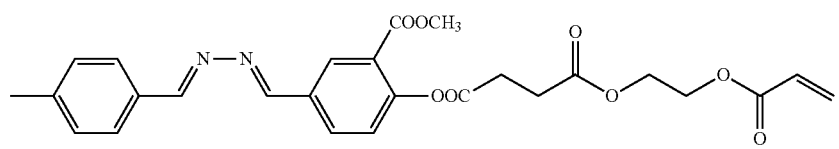

Step 1: Synthesis of Intermediate (a)

[Chemical formula 16]

Intermediate (a)

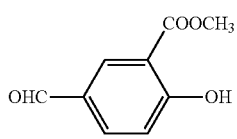

In a four-neck reactor provided with a condenser, a thermometer and a dropping funnel, under a nitrogen flow, 15 g of 5-formylsalicylic acid (0.09 mol), 14.5 g of methanol (0.45 mol) and 4-(dimethylamino)pyridine were dissolved in 200 ml of tetrahydrofuran (hereinafter, it will be simply referred to as "THF"). To the thus-obtained solution, under room temperature, 37.3 g of N,N-dicyclohexylcarbodiimide (0.18 mol) dissolved in 100 ml of THF was gradually added with a dropping funnel. Then, the resultant was reacted for 6 hours under room temperature. After the reaction, the resultant was filtered under reduced pressure. Then, THF was removed with a rotary evaporator under reduced pressure to obtain yellow oil. This yellow oil was purified by silica gel column chromatography (n-hexane:THF=9:1), thereby obtaining 13.4 g of white solid (intermediate (a)) (yield: 82.4%). The structure was identified by $^1$H-NMR.

($^1$H-NMR data of intermediate (a))

$^1$H-NMR (500 MHz, CDCl$_3$, TMS, δ ppm): 11.36 (s, 1H), 9.88 (s, 1H), 8.39 (s, 1H), 8.00 (d, 1H, J=9.0 Hz), 7.11 (d, 1H, J=9.0 Hz), 4.01 (s, 3H).

Step 2: Synthesis of Intermediate (b)

[Chemical formula 17]

Intermediate (b)

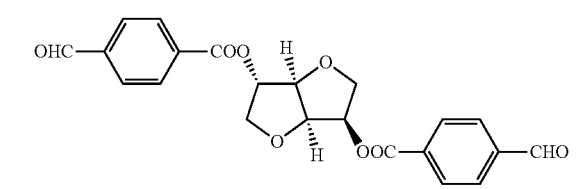

in a four-neck reactor provided with a thermometer, under a nitrogen flow, 86.3 g of terephthalaldehydic acid (0.57 mol), 40 g of isosorbide (0.23 mol) and 7.0 g of 4-(dimethylamino) pyridine (0.057 mol) were dissolved in 650 ml of N-methylpyrrolidone. To the thus-obtained solution, in a water bath, 110.2 g of 1-ethyl-3-(3-dimethylaminopropyl)carbodiimide hydrochloride (WSC) (0.57 mol) was gradually added. Then, the resultant was reacted for 15 hours under room temperature. After the reaction, the reaction solution was mixed with water and then extracted twice with 500 ml of ethyl acetate. After a water layer was removed by separation, the thus-obtained ethyl acetate layer was dried over anhydrous magnesium sulfate and then filtered under reduced pressure to remove magnesium sulfate. The ethyl acetate layer was condensed with a rotary evaporator under reduced pressure to obtain light yellow oil. The thus-obtained oil was purified by silica gel column chromatography (n-hexane:THF=3:2), thereby obtaining 38 g of white solid (intermediate (b)) (yield: 40.3%). The structure was identified by $^1$H-NMR.

($^1$H-NMR data of intermediate (b))

$^1$H-NMR (500 MHz, CDCl$_3$, TMS, δ ppm): 10.13 (s, 1H), 10.11 (s, 1H), 8.26 (d, 2H, J=8.0 Hz), 8.19 (d, 2H, J=8.0 Hz), 8.00 (d, 2H, J=8.0 Hz), 7.97 (d, 2H, J=8.0 Hz), 5.53 (s, 1H), 5.48 (q, 1H, J=5.0 Hz, J=10.5 Hz), 5.12 (t, 1H, J=5.0 Hz), 4.72 (d, 1H, J=5.0 Hz), 4.15-4.10 (m, 4H).

Step 3: Synthesis of Intermediate (c)

In a four-neck reactor provided with a thermometer, under a nitrogen flow, 2.3 g of hydrazine monohydrate (0.046 mol) was dissolved in 80 ml of ethanol. To the thus-obtained solution, under room temperature, 8.2 g of the intermediate (a) (0.046 mol) was added and agitated for 30 minutes at room temperature. Then, 9.3 g of the intermediate (b) (0.023 mol) was dissolved in 80 ml of THF, added to the above-obtained solution, and reacted for 4 hours at room temperature. A crystal thus precipitated was collected by filtration and rinsed with ethanol to obtain 9.0 g of yellow solid comprising an intermediate (c). The yellow solid comprising the intermediate (c) had low solubility in solvents that can be used for purification, so that purification was difficult to perform. Therefore, the yellow solid was used as it is in the next step.

Step 4: Synthesis of Polymerizable Chiral Compound (I-1)

In a four-neck reactor provided with a thermometer, under a nitrogen flow, 7.0 g of the yellow solid comprising the intermediate (c) synthesized in the above Step 3, 4.6 g of 2-(acryloyloxy)ethyl hydrogen succinate (21.3 mmol) and 0.26 g of 4-(dimethylamino)pyridine (2.1 mmol) were dissolved in 200 ml of N,N-dimethylformamide (hereinafter, it will be simply referred to as "DMF"). To the thus-obtained solution, under room temperature, 4.1 g of 1-ethyl-3-(3-dimethylaminopropyl)carbodiimide hydrochloride (WSC) (21.4 mmol) was added. Then, the resultant was reacted for 18 hours under room temperature. After the reaction, the reaction solution was mixed with water and then extracted twice with 200 ml of ethyl acetate. After a water layer was removed by separation, the thus-obtained ethyl acetate layer was dried over anhydrous magnesium sulfate and then filtered to remove magnesium sulfate. The ethyl acetate layer was condensed with a rotary evaporator to obtain yellow oil. The thus-obtained yellow oil was purified by silica gel column chromatography (n-hexane:THF=5:5), thereby obtaining 2.3 g of a polymerizable chiral compound (I-1) in the form of light yellow solid. The structure was identified by $^1$H-NMR.

[Chemical formula 18]

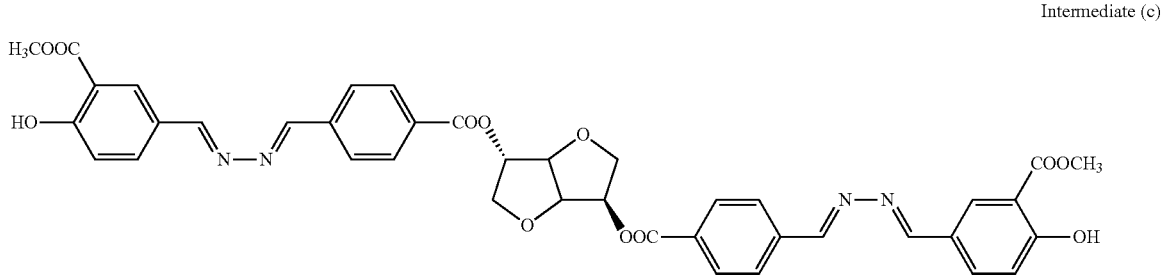

Intermediate (c)

($^1$H-NMR data of polymerizable chiral compound (I-1))

$^1$H-NMR (500 MHz, CDCl$_3$, TMS, δ ppm): 8.71 (s, 1H), 8.69 (s, 1H), 8.68 (s, 1H), 8.68 (s, 1H), 8.48-8.47 (m, 2H), 8.18 (d, 2H, J=8.5 Hz), 8.12-8.07 (m, 4H), 7.96-7.92 (m, 4H), 7.24 (dd, 2H, J=1.5 Hz, J=8.5 Hz), 6.44 (dd, 2H, J=1.3 Hz, J=17.3 Hz), 6.14 (dd, 2H, J=10.5 Hz, 17.3 Hz), 5.86 (dd, 2H, J=1.3 Hz, J=10.5 Hz), 5.53 (s, 1H), 5.47 (q, 1H, J=5.0 Hz, J=10.5 Hz), 5.12 (t, 1H, J=5.0 Hz), 4.73 (d, 1H, J=5.0 Hz), 4.39 (s, 8H), 4.15-4.14 (m, 2H), 4.11 (d, 2H, J=5.0 Hz), 3.92 (s, 6H), 3.02 (t, 4H, J=7.0 Hz), 2.83 (t, 4H, J=7.0 Hz).

Example 2

Synthesis of Polymerizable Chiral Compound (I-2)

[Chemical formula 19]

Compound (I-2)

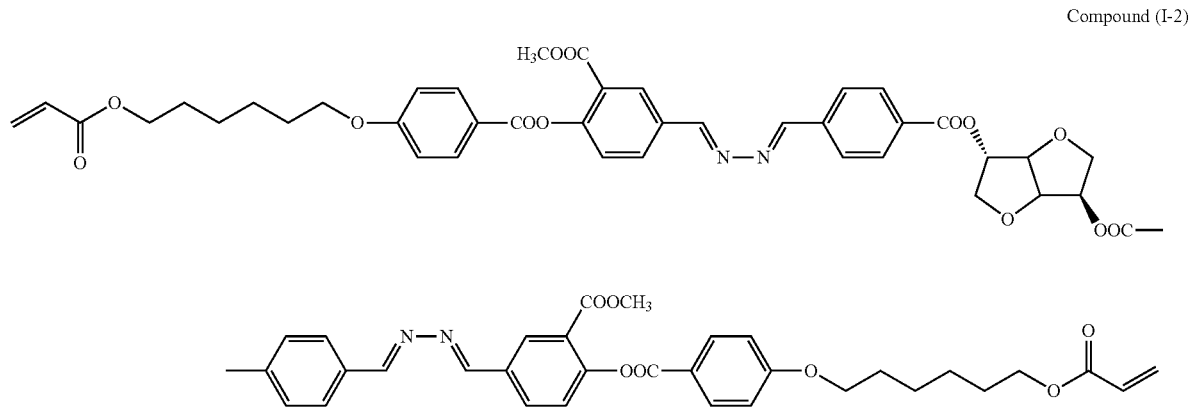

A reaction and posttreatment were performed in the same manner as the synthesis of the polymerizable chiral compound (I-1) except that 4-(6-acryloyl-hex-1-yloxy)benzoic acid (manufactured by: Nihon Siber Hegner K.K.) was used in the step 4 instead of 2-(acryloyloxy)ethyl hydrogen succinate. The thus-obtained reaction mixture was purified by silica gel column chromatography (n-hexane:THF=5:5), thereby obtaining a polymerizable chiral compound (I-2). The structure was identified by $^1$H-NMR.

($^1$H-NMR data of polymerizable chiral compound (I-2))
$^1$H-NMR (400 MHz, CDCl$_3$, TMS, δ ppm): 8.68 (m, 4H), 8.48 (s, 2H), 8.16-8.08 (m, 10H), 7.92 (t, 4H, J=9.0 Hz), 7.33 (d, 2H, J=8.2 Hz), 6.97 (d, 4H, J=8.2 Hz), 6.38 (d, 2H, J=17.4 Hz), 6.13 (dd, 2H, J=10.1 Hz, J=17.4 Hz), 5.81 (d, 2H, J=10.1 Hz), 5.51 (s, 1H), 5.45 (dd, 1H, J=5.0 Hz, J=10.5 Hz), 5.09 (t, 1H, J=5.0 Hz), 4.71 (d, 1H, J=4.6 Hz), 4.19-3.99 (m, 12H), 3.77 (s, 6H), 1.83-1.45 (m, 16H).

Example 3

Synthesis of Polymerizable Chiral Compound (I-3)

[Chemical formula 20]

Compound (I-3)

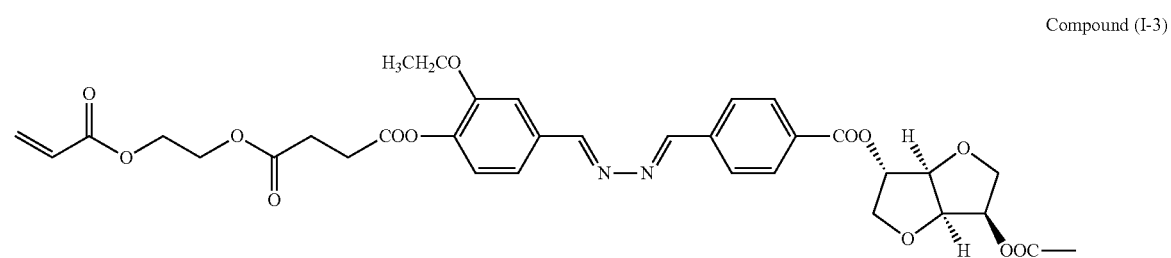

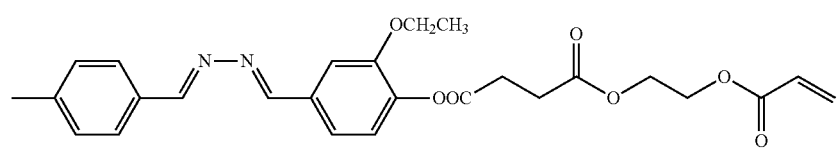

Step 1: Synthesis of Intermediate (d)

[Chemical formula 21]

Intermediate (d)

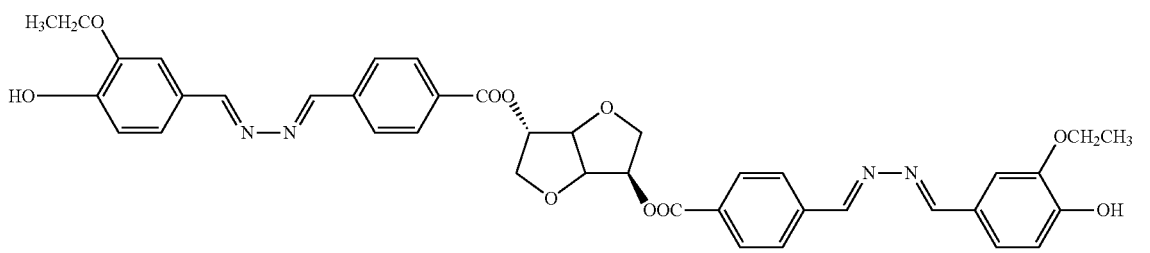

A reaction was performed in the same manner as the synthesis of the polymerizable chiral compound (I-1) except that ethyl vanillin (3-ethoxy-4-hydroxybenzaldehyde) was used in the step 3 instead of the intermediate (a), thereby obtaining yellow solid comprising an intermediate (d). The thus-obtained yellow solid comprising the intermediate (d) was used as it is in the next step without purification.

Step 2: Synthesis of Polymerizable Chiral Compound (I-3)

In a four-neck reactor provided with a thermometer, under a nitrogen flow, 3.0 g of the yellow solid comprising the intermediate (d) obtained in the above Step 1, 2.0 g of 2-(acryloyloxy)ethyl hydrogen succinate (9.25 mmol), and 0.05 g of 4-(dimethylamino)pyridine (0.4 mmol) were dissolved in 200 ml of DMF. To the thus-obtained solution, under room temperature, 4.1 g of 1-ethyl-3-(3-dimethylaminopropyl)carbodiimide hydrochloride (WSC) (21.4 mmol) was added. Then, the resultant was reacted for 18 hours under room temperature. After the reaction, the reaction solution was mixed with water and then extracted twice with 200 ml of ethyl acetate. After a water layer was removed by separation, the thus-obtained ethyl acetate layer was dried over anhydrous magnesium sulfate and then filtered to remove magnesium sulfate. The ethyl acetate layer was condensed with a rotary evaporator to obtain yellow oil. The thus-obtained oil was purified by silica gel column chromatography (chloroform:ethyl acetate=95:5), thereby obtaining 0.72 g of a polymerizable chiral compound (I-3) in the form of yellow solid. The structure was identified by $^1$H-NMR.

($^1$H-NMR data of polymerizable chiral compound (I-3))

$^1$H-NMR (400 MHz, CDCl$_3$, TMS, δ ppm): 8.66 (d, 2H, J=6.0), 8.59-8.55 (m, 2H), 8.16-8.05 (m, 4H), 7.90 (t, 4H, J=8.0 Hz), 7.56 (s, 2H), 7.30-7.20 (m, 2H), 7.12 (m, 2H), 6.42 (d, 2H, J=17.4 Hz), 6.12 (dd, 2H, J=10.1 Hz, J=17.4 Hz), 5.84 (d, 2H, J=10.1 Hz), 5.52 (s, 1H), 5.46 (dd, 1H, J=5.5 Hz, J=10.5 Hz), 5.10 (t, 1H, J=5.5 Hz), 4.71 (d, 1H, J=4.2 Hz), 4.40-4.05 (m, 16H), 3.00-2.75 (m, 8H), 1.42 (t, 6H, J=6.9 Hz).

Example 4

Synthesis of Polymerizable Chiral Compound (I-4)

[Chemical formula 22]

Compound (I-4)

In a four-neck reactor provided with a thermometer and a dropping funnel, under a nitrogen flow, 2.7 g of 4-(6-acryloylhex-1-yloxy)benzoic acid (manufactured by: Nihon Siber Hegner K.K.) (9.24 mmol) and 1.1 g of methanesulfonyl chloride (9.6 mmol) were dissolved in 50 ml of THF. After cooling the thus-obtained solution in an ice bath, 1.0 g of triethylamine (9.88 mmol) was added dropwise thereto for 30 minutes and then reacted for 1 hour at the same temperature. Next, to the reaction solution, 3.0 g of the above-obtained yellow solid comprising the intermediate (d) and 0.12 g of 4-(dimethylamino)pyridine (0.98 mmol) were added. Then, in an ice bath, 1.0 g of triethylamine (9.88 mmol) was added dropwise thereto for 30 minutes. After the addition, the resultant was reacted further for 4 hours at room temperature. After the reaction, 150 ml of methanol was added to the reaction solution for 1 hour. A precipitate thus deposited was collected by filtration and washed with methanol. The thus-obtained precipitate was dissolved in chloroform and purified by silica gel column chromatography (chloroform:ethyl acetate=95:5), thereby obtaining 0.56 g of a polymerizable chiral compound (1-4) in the form of yellow solid. The structure was identified by $^1$H-NMR.

($^1$H-NMR data of Polymerizable Chiral Compound (I-4))
$^1$H-NMR (400 MHz, CDCl$_3$, TMS, δ ppm): 8.53 (d, 2H, J=6.0 Hz), 8.49 (d, 2H, J=2.8 Hz), 8.02-7.94 (m, 8H), 7.77 (t, 4H, J=9.2 Hz), 7.46 (s, 2H), 7.21 (d, 2H, J=8.2 Hz), 7.09 (m, 2H), 6.82 (d, 4H, J=8.7 Hz), 6.40 (d, 2H, J=17.4 Hz), 6.12 (dd, 2H, J=10.1 Hz, J=17.4 Hz), 5.83 (d, 2H, J=10.1 Hz), 5.53 (s, 1H), 5.46 (dd, 1H, J=5.5 Hz, J=10.5 Hz), 5.10 (t, 1H, J=5.5 Hz), 4.72 (d, 1H, J=4.6 Hz), 4.20-4.06 (m, 16H), 1.83-1.45 (m, 22H).

Example 5

Synthesis of Polymerizable Chiral Compound (I-5)

[Chemical formula 23]

Compound (I-5)

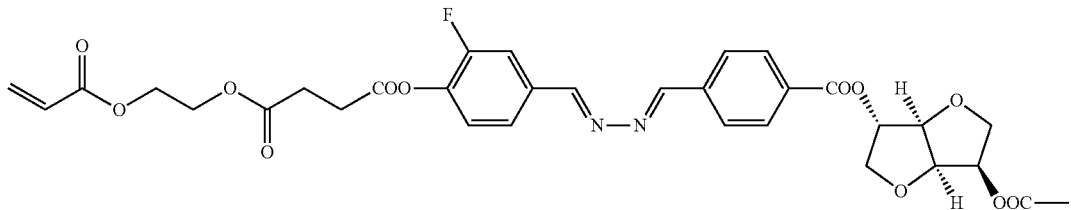

Step 1: Synthesis of Intermediate (e)

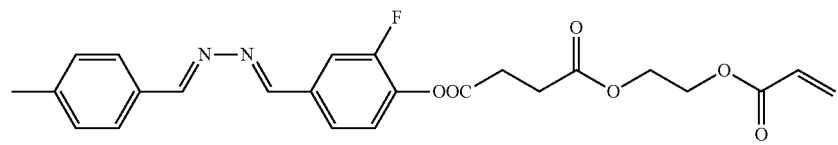

[Chemical formula 24]

Intermediate (e)

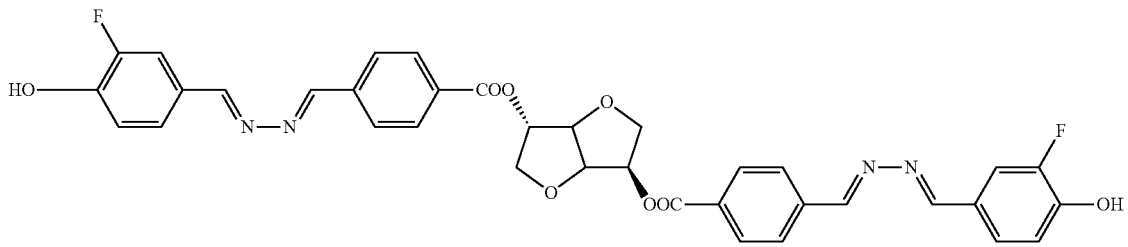

A reaction was performed in the same manner as the synthesis of the polymerizable chiral compound (I-1) except that 3-fluoro-4-hydroxybenzaldehyde was used in the step 3 instead of the intermediate (a), thereby obtaining yellow solid comprising an intermediate (e). The thus-obtained yellow solid comprising the intermediate (e) was used as it is in the next step without purification.

Step 2: Synthesis of Polymerizable Chiral Compound (I-5)

A reaction and posttreatment were performed in the same manner as the synthesis of the polymerizable chiral compound (I-3) except that the yellow solid comprising the intermediate (e) obtained in the above step 1 was used in the step 2 instead of the yellow solid comprising the intermediate (d). The thus-obtained reaction mixture was purified by silica gel column chromatography (chloroform:ethyl acetate=95:5), thereby obtaining a polymerizable chiral compound (I-5) in the form of yellow solid. The structure was identified by $^1$H-NMR.

($^1$H-NMR data of polymerizable chiral compound (I-5))
$^1$H-NMR (400 MHz, CDCl$_3$, TMS, δ ppm): 8.68 (d, 2H, J=6.0 Hz), 8.63 (d, 2H, J=2.3 Hz), 8.15 (d, 2H, J=8.2 Hz), 8.09 (d, 2H, J=8.2 Hz), 7.92 (t, 4H, J=9.0 Hz), 7.73 (d, 2H, J=10.6 Hz), 7.56 (d, 2H, J=8.2 Hz), 7.27 (m, 2H), 6.42 (d, 2H, J=17.4 Hz), 6.12 (dd, 2H, J=10.1 Hz, J=17.4 Hz), 5.84 (d, 2H, J=10.1 Hz), 5.52 (s, 1H), 5.45 (dd, 1H, J=5.2 Hz, J=10.8 Hz), 5.10 (t, 1H, J=5.0 Hz), 4.71 (d, 1H, J=4.6 Hz), 4.37 (s, 8H), 4.10-4.08 (m, 4H), 3.00-2.75 (m, 8H).

Example 6

Synthesis of Polymerizable Chiral Compound (I-6)

[Chemical formula 25]

Compound (I-6)

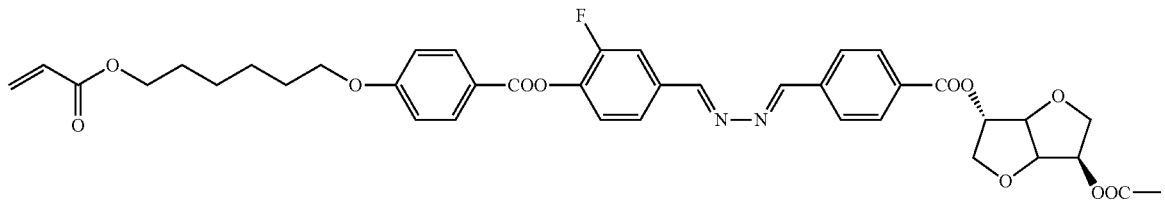

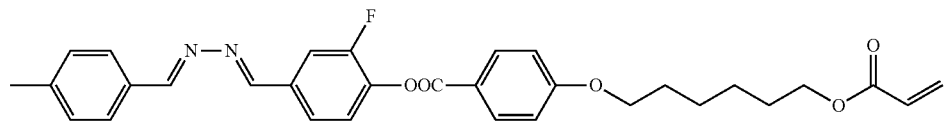

A reaction and posttreatment were performed in the same manner as the synthesis of the polymerizable chiral compound (I-4) except that the above-obtained yellow solid comprising the intermediate (e) was used instead of the yellow solid comprising the intermediate (d). The thus-obtained reaction mixture was purified by silica gel column chromatography (chloroform:ethyl acetate=95:5), thereby obtaining a polymerizable chiral compound (I-6). The structure was identified by $^1$H-NMR.

($^1$H-NMR data of polymerizable chiral compound (I-6))
$^1$H-NMR (400 MHz, CDCl$_3$, TMS, δ ppm): 8.68 (d, 2H, J=6.0 Hz), 8.63 (d, 2H, J=2.3 Hz), 8.18-8.09 (m, 8H), 7.93 (t, 4H, J=9.2 Hz), 7.78 (d, 2H, J=10.5 Hz), 7.62 (d, 2H, J=8.2 Hz), 7.36 (d, 2H, J=8.2 Hz), 6.98 (d, 4H, J=8.7 Hz), 6.40 (d, 2H, J=17.4 Hz), 6.12 (dd, 2H, J=10.1 Hz, J=17.4 Hz), 5.81 (d, 2H, J=10.1 Hz), 5.53 (s, 1H), 5.46 (dd, 1H, J=5.5, J=10.2 Hz), 5.10 (t, 1H, J=5.5 Hz), 4.72 (d, 1H, J=4.6 Hz), 4.20-4.04 (m, 12H), 1.83-1.45 (m, 16H).

Example 7

Synthesis of Polymerizable Chiral Compound (I-7)

[Chemical formula 26]

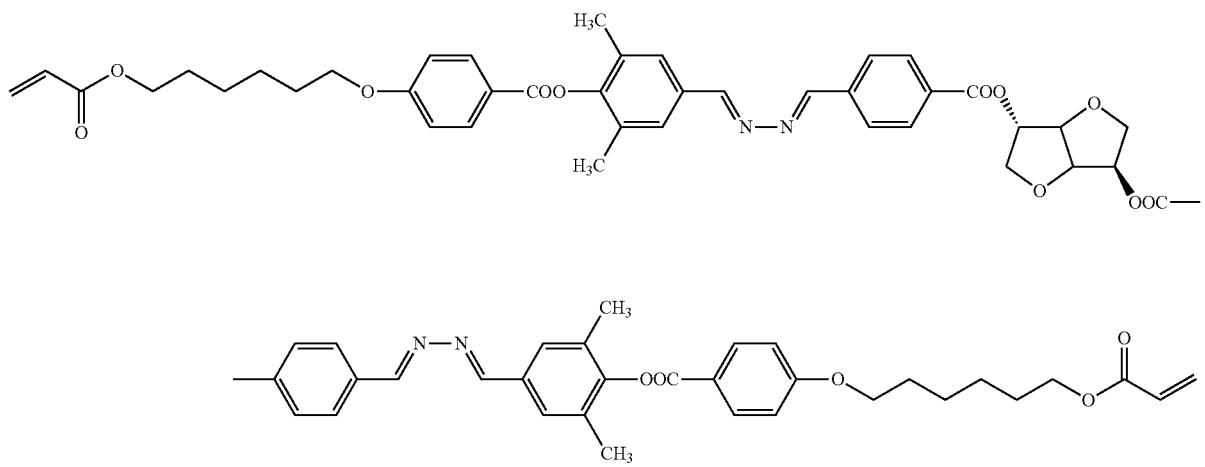

Compound (I-7)

Step 1: Synthesis of Intermediate (f)

[Chemical formula 27]

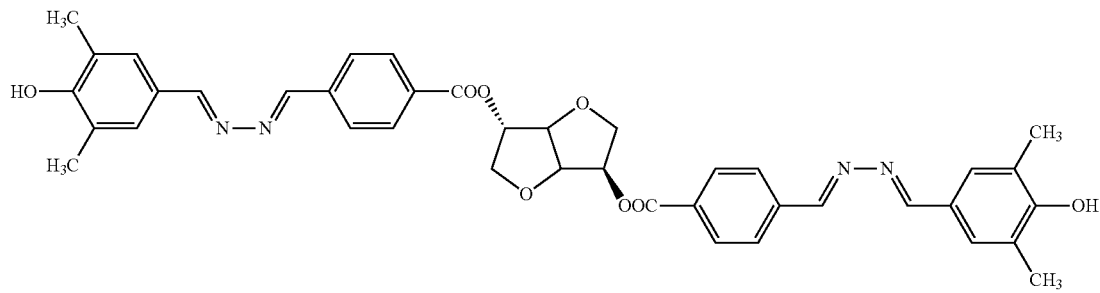

Intermediate (f)

A reaction was performed in the same manner as the synthesis of the polymerizable chiral compound (I-1) except that 4-hydroxy-3,5-dimethylbenzaldehyde was used instead of the intermediate (a), thereby obtaining yellow solid comprising an intermediate (f). The yellow solid comprising the intermediate (f) was used as it is in the next step without purification.

Step 2: Synthesis of Polymerizable Chiral Compound (I-7)

A reaction and posttreatment were performed in the same manner as the synthesis of the polymerizable chiral compound (I-4) except that the above-obtained yellow solid comprising the intermediate (f) was used instead of the yellow solid comprising the intermediate (d). The thus-obtained reaction mixture was purified by silica gel column chromatography (chloroform:ethyl acetate=95:5) thereby obtaining a polymerizable chiral compound (I-7). The structure was identified by $^1$H-NMR.

($^1$H-NMR data of polymerizable chiral compound (I-7))
$^1$H-NMR (400 MHz, CDCl$_3$, TMS, δ ppm): 8.70 (d, 2H, J=6.0 Hz), 8.64 (d, 2H, J=2.7 Hz), 8.21-8.09 (m, 8H), 7.93 (t, 4H, J=9.2 Hz), 7.64 (s, 4H), 6.98 (d, 4H, J=8.7 Hz), 6.40 (d, 2H, J=17.4 Hz), 6.12 (dd, 2H, J=10.1 Hz, J=17.4 Hz), 5.81 (d, 2H, J=10.1 Hz), 5.54 (s, 1H), 5.47 (dd, 1H, J=5.2 Hz, J=10.5 Hz), 5.11 (t, 1H, J=5.0 Hz), 4.73 (d, 1H, J=4.6 Hz), 4.20-4.04 (m, 12H), 2.26 (s, 12H), 1.83-1.45 (m, 16H).

(Measurement of Helical Twisting Power (HTP))

One surface of a ZEONOR film (product name: ZE16-100; manufactured by: Optes Inc.) was subjected to corona discharge treatment. Then, a 5% by mass aqueous solution of polyvinyl alcohol (product name: POVAL MP203; manufactured by: Kuraray Co., Ltd) was applied onto the surface, dried for 3 minutes at 100° C., and then rubbed with a felt roller to form an alignment film. Thereby, a substrate was obtained.

A solution was prepared by dissolving 100 parts of a polymerizable liquid crystal compound in 153 parts of cyclopentanone. To the thus-obtained solution, 3.3 parts of a photo polymerization initiator (product name: Irgacure 1919; manufactured by: Chiba Specialty Chemicals, Inc.), 6.5 parts of a chiral agent, and 11.7 parts of a surfactant (used as a 1% by weight cyclopentanone solution) were added and dissolved completely, thereby preparing a polymerizable liquid crystal composition.

As the chiral agent, the polymerizable chiral compounds (I-1) to (I-7) synthesized in Examples 1 to 7 were used each.

As the polymerizable liquid crystal compound, a compound produced by the method disclosed in Japanese Patent Application No. 2008-92093 (a compound represented by the following formula (LC)) was used.

As the surfactant, a surfactant (product name: KH-40; manufactured by AGC SEIMI CHEMICAL CO., LTD.) was used.

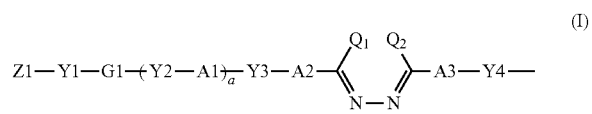

[Chemical formula 28]

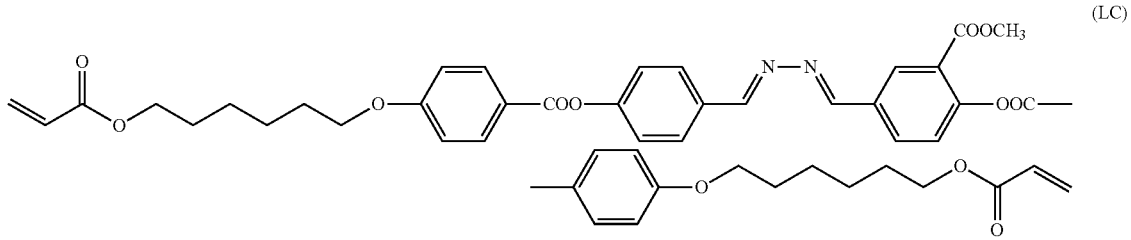

Next, the above-obtained polymerizable liquid crystal composition was filtered with a syringe filter of polytetrafluoroethylene having a pore diameter of 0.45 μm to obtain a sample. The thus-obtained sample was applied onto the alignment film of the substrate and dried for 2 minutes at 135° C. to form a coating film.

Next, the thus-obtained coating film was exposed to ultraviolet light at 2,000 mJ/cm² emitted from a mercury lamp, thereby forming a cholesteric polymer cured film having a thickness of about 5 μm.

The center value λ (μm) in the selective reflection band of the cholesteric polymer cured film was measured with a spectral photometer (product name: Multi Channel Photo Detector MCPD-3000; manufactured by: Otsuka Electronics Co., Ltd.) and the helical twisting power (HTP) was calculated by the following formula:

Formula: HTP=$n/(\lambda \times C)$ [Mathematical formula 1]

wherein C represents the concentration of the chiral agent in a polymerizable liquid crystal compound (part by mass/100); and n represents the average refractive index of the polymerizable liquid crystal compound. The results are shown in Table 1.

TABLE 1

| Polymerizable chiral compound | HTP (/μm) |
|---|---|
| I-1 | 32.0 |
| I-2 | 46.5 |
| I-3 | 32.2 |
| I-4 | 47.0 |
| I-5 | 25.5 |
| I-6 | 29.6 |
| I-7 | 42.7 |

The results in Table 1 show that the polymerizable chiral compounds (I-1) to (I-7) of Examples 1 to 7 have high helical twisting power (HTP).

The invention claimed is:

1. A polymerizable chiral compound represented by the following formula (I):

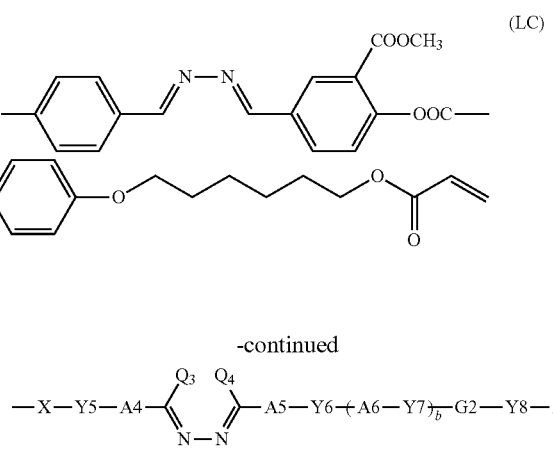

wherein Y1 to Y8 are each independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$— or —NR$^1$—O—, and R$^1$ is a hydrogen atom or an alkyl group having 1 to 6 carbon atoms;

wherein G1 and G2 are each independently a divalent aliphatic group having 1 to 20 carbon atoms, which may have a substituent; the aliphatic group may contain —O—, —S—, —O—C(=O)—, —C(=O)—O—, —O—C(=O)—O—, —NR$^2$—C(=O)—, —C(=O)—NR$^2$—, —NR$^2$— or —C(=O)— unless two or more —O— are adjacent as well as two or more —S—; R$^2$ is a hydrogen atom or an alkyl group having 1 to 6 carbon atoms; and Z1 and Z2 are each independently an alkenyl group having 2 to 10 carbon atoms, which may be substituted by a halogen atom;

wherein Q$_1$ to Q$_4$ are each independently a hydrogen atom or an alkyl group having 1 to 6 carbon atoms, which may have a substituent;

wherein A1 to A6 are each independently a divalent aromatic group A having 6 to 30 carbon atoms;

wherein X is any of groups represented by the following (X-i) to (X-vi):

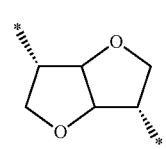

(X-i)

-continued

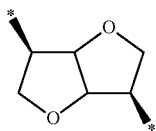
(X-ii)

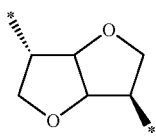
(X-iii)

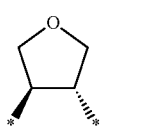
(X-iv)

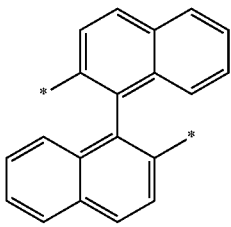
(X-v)

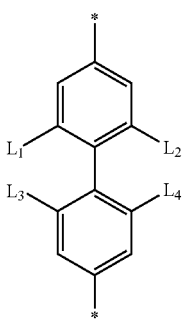
(X-vi)

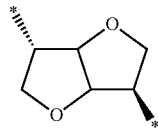
(X-iii)

wherein * represents a bond.

5. The polymerizable chiral compound according to claim 1,
in the formula (I), wherein Y1 to Y8 are each independently —C(=O)—O—, —O—C(=O)— or —O—;
wherein G1 and G2 are each independently —(CH$_2$)$_6$— or —(CH$_2$)$_4$—, which may contain —O—, —C(=O)—O—, —O—C(=O)— or —C(=O)—;
wherein Z1 and Z2 are each independently CH$_2$=CH—, CH$_2$=C(CH$_3$)— or CH$_2$=C(Cl)—; and
wherein A1 to A6 are each independently any of groups represented by the following (A-i), (A-ii) and (A-iii):

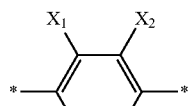
(A-i)

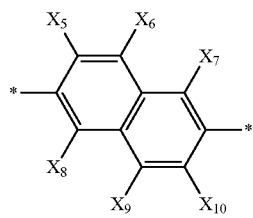
(A-ii)

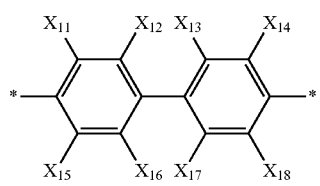
(A-iii)

wherein * represents a bond; $X_1$ to $X_{18}$ are each independently a hydrogen atom, a halogen atom, an alkyl group having 1 to 10 carbon atoms, which may have a substituent, a cyano group, a nitro group, —OR$^4$, —O—C(=O)—R$^4$, —C(=O)—OR$^4$, —O—C(=O)—OR$^4$, —NR$^5$—C(=O)—R$^4$, —C(=O)—N(R$^4$)R$^5$ or —O—C(=O)—N(R$^4$)R$^5$; R$^4$ and R$^5$ are each independently a hydrogen atom or an alkyl group having 1 to 10 carbon atoms, which may have a substituent; with the provision that if R$^4$ and/or R$^5$ is an alkyl group, the alkyl group may contain —O—, —S—, —O—C(=O)—, —C(=O)—O—, —O—C(=O)—O—, —NR$^6$—C(=O)—, —C(=O)—NR$^6$—, —NR$^6$— or —C(=O)— unless two or more —O— are adjacent as well as two or more —S—; and R$^6$ is a hydrogen atom or an alkyl group having 1 to 6 carbon atoms.

wherein * represents a bond; $L_1$ to $L_4$ are each independently an alkyl group having 1 to 4 carbon atoms, an alkoxy group having 1 to 4 carbon atoms, a halogen atom, —COOR$^3$, —OCOR$^3$, —OCOOR$^3$, —CONHR$^3$ or NHCOR$^3$; and R$^3$ is a hydrogen atom or an alkyl group having 1 to 6 carbon atoms;
and wherein, in the formula (I), a and b are each independently 0 or 1.

2. The polymerizable chiral compound according to claim 1, wherein A1 to A6 of the formula (I) are each independently a phenylene group which may have a substituent, a biphenylene group which may have a substituent, or a naphthylene group which may have a substituent.

3. The polymerizable chiral compound according to claim 1, wherein Z1 and Z2 of the formula (I) are each independently CH$_2$=CH—, CH$_2$=C(CH$_3$)—, CH$_2$=C(Cl)—, CH$_2$=CH—CH$_2$—, CH$_2$=C(CH$_3$)—CH$_2$—, CH$_2$=C(CH$_3$)—CH$_2$CH$_2$—, (CH$_3$)$_2$C=CH—CH$_2$—, CH$_3$—CH=CH— or CH$_3$—CH=CH—CH$_2$—.

4. The polymerizable chiral compound according to claim 1, wherein X of the formula (I) is the following (X-iii):

6. The polymerizable chiral compound according to claim 1,
in the formula (I), wherein Y1 to Y8 are each independently —C(=O)—O—, —O—C(=O)— or —O—;

wherein G1 and G2 are each independently —(CH$_2$)$_6$— or —(CH$_2$)$_4$—;

wherein Z1 and Z2 are each independently CH$_2$=CH— or CH$_2$=C(CH$_3$)—; and wherein A1 to A6 are each independently a group represented by the following (A-i):

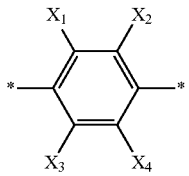

(A-i)

wherein * represents a bond; X1 to X4 are each independently a hydrogen atom, a halogen atom, an alkyl group having 1 to 10 carbon atoms, which may have a substituent, a cyano group, a nitro group, —OR$^4$, —O—C(=O)—R$^4$, —C(=O)—OR$^4$, —O—C(=O)—OR$^4$, —NR$^5$—C(=O)—R$^4$, —C(=O)—N(R$^4$)R$^5$ or —O—C(=O)—N(R$^4$)R$^5$; R$^4$ and R$^5$ are each independently a hydrogen atom or an alkyl group having 1 to 10 carbon atoms, which may have a substituent; with the provision that if R$^4$ and/or R$^5$ is an alkyl group, the alkyl group may contain —O—, —S—, —O—C(=O)—, —C(=O)—O—, —O—C(=O)—O—, —NR$^6$—C(=O)—, —C(=O)—NR$^6$—, —NR$^6$— or C(=O)— unless two or more —O— are adjacent as well as two or more —S—; and R$^6$ is a hydrogen atom or an alkyl group having 1 to 6 carbon atoms.

7. The polymerizable chiral compound according to claim 1,
in the formula (I), wherein Y1 to Y8 are each independently —C(=O)—O—, —O—C(=O)— or —O—;
wherein G1 and G2 are each independently —(CH$_2$)$_6$— or —(CH$_2$)$_4$—;
wherein Z1 and Z2 are CH$_2$=CH—;
wherein Q$_1$ to Q$_4$ are each independently a hydrogen atom or a methyl group; and
wherein A1 to A6 are each independently a group represented by the following (A-i):

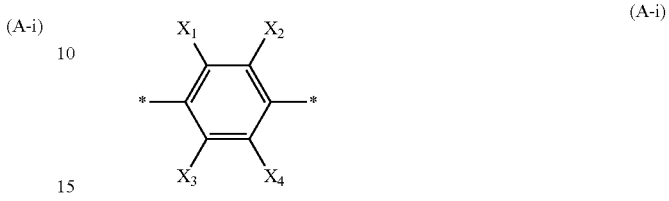

(A-i)

wherein * represents a bond; X$_1$ to X$_4$ are each independently a hydrogen atom, a halogen atom, an alkyl group having 1 to 10 carbon atoms, which may have a substituent, a cyano group, a nitro group, —OR$^4$, —O—C(=O)—R$^4$ or —C(=O)—OR$^4$; R$^4$ is a hydrogen atom or an alkyl group having 1 to 10 carbon atoms, which may have a substituent; and with the provision that if R$^4$ is an alkyl group, the alkyl group may contain —O—, —S—, —O—C(=O)—, —C(=O)—O— or C(=O)— unless two or more —O— are adjacent as well as two or more —S—.

8. A polymerizable liquid crystal composition comprising the polymerizable chiral compound defined by claim 1 and a polymerizable liquid crystal compound.

9. A liquid crystal polymer obtained by polymerization of the polymerizable liquid crystal composition defined by claim 8.

10. An optically anisotropic body comprising the liquid crystal polymer defined by claim 9 as a constitutional material.

* * * * *